US012161462B2

(12) United States Patent
Peterson et al.

(10) Patent No.: US 12,161,462 B2
(45) Date of Patent: Dec. 10, 2024

(54) SUBCUTANEOUS ANALYTE SENSOR APPLICATOR AND CONTINUOUS MONITORING SYSTEM

(71) Applicant: SANVITA MEDICAL CORPORATION, Waltham, MA (US)

(72) Inventors: Thomas H. Peterson, Wilmington, MA (US); Jonathan Scott, Hollis, NH (US); Anthony Florindi, Norfolk, MA (US); Sten P. Kaeding, Worcester, VT (US); Mauro Dellemonache, Dedham, MA (US)

(73) Assignee: SANVITA MEDICAL CORPORATION, Waltham, MA (US)

( * ) Notice: Subject to any disclaimer, the term of this patent is extended or adjusted under 35 U.S.C. 154(b) by 554 days.

(21) Appl. No.: 17/607,071

(22) PCT Filed: May 14, 2019

(86) PCT No.: PCT/US2019/032114
§ 371 (c)(1),
(2) Date: Oct. 28, 2021

(87) PCT Pub. No.: WO2020/231405
PCT Pub. Date: Nov. 19, 2020

(65) Prior Publication Data
US 2022/0225899 A1 Jul. 21, 2022

(51) Int. Cl.
*A61B 5/145* (2006.01)
*A61B 5/00* (2006.01)
*A61B 5/1473* (2006.01)

(52) U.S. Cl.
CPC ........ *A61B 5/14503* (2013.01); *A61B 5/0031* (2013.01); *A61B 5/14532* (2013.01);
(Continued)

(58) Field of Classification Search
None
See application file for complete search history.

(56) References Cited

U.S. PATENT DOCUMENTS

2012/0190943 A1  7/2012  Donnay et al.
2014/0187876 A1  7/2014  Ohkoshi
(Continued)

FOREIGN PATENT DOCUMENTS

CN  107949314 A  4/2018
EP  3202324 A1  8/2017
(Continued)

*Primary Examiner* — Jay B Shah
(74) *Attorney, Agent, or Firm* — Hayes Soloway PC

(57) ABSTRACT

A subcutaneous analyte sensor applicator includes an inserter module and a sensor module. The inserter module includes an applicator housing, a deployment button, and a pre-loaded insertion assembly completely disposed and secured within the button and partially disposed within the applicator housing when the button is in an initial, loaded position on the applicator housing. The insertion assembly includes an assembly housing, and a biasing element and a needle assembly disposed within the assembly housing chamber where the biasing element is in a compressed state. The sensor module includes a sensor lower housing releasably connected to the applicator housing, a sensor upper housing removably retained against the insertion assembly housing and spaced from the sensor lower housing, and an electro-sensor assembly disposed within the sensor upper housing where a sensor is temporarily disposed within a needle of a needle assembly when the applicator system is in the initial pre-loaded position.

17 Claims, 21 Drawing Sheets

(52) U.S. Cl.
CPC .......... *A61B 5/1473* (2013.01); *A61B 5/6848* (2013.01); *A61B 5/688* (2013.01); *A61B 2560/063* (2013.01)

(56) References Cited

U.S. PATENT DOCUMENTS

| | | | |
|---|---|---|---|
| 2016/0030078 A1 | 2/2016 | Lee et al. | |
| 2016/0058474 A1* | 3/2016 | Peterson | A61B 5/686 600/347 |
| 2016/0310051 A1* | 10/2016 | Brister | A61B 5/1411 |

FOREIGN PATENT DOCUMENTS

| | | | |
|---|---|---|---|
| JP | 2008237921 A | 10/2008 | |
| WO | 2018118061 A1 | 6/2018 | |
| WO | 2018222012 A1 | 12/2018 | |
| WO | 2020231405 A1 | 11/2020 | |

* cited by examiner

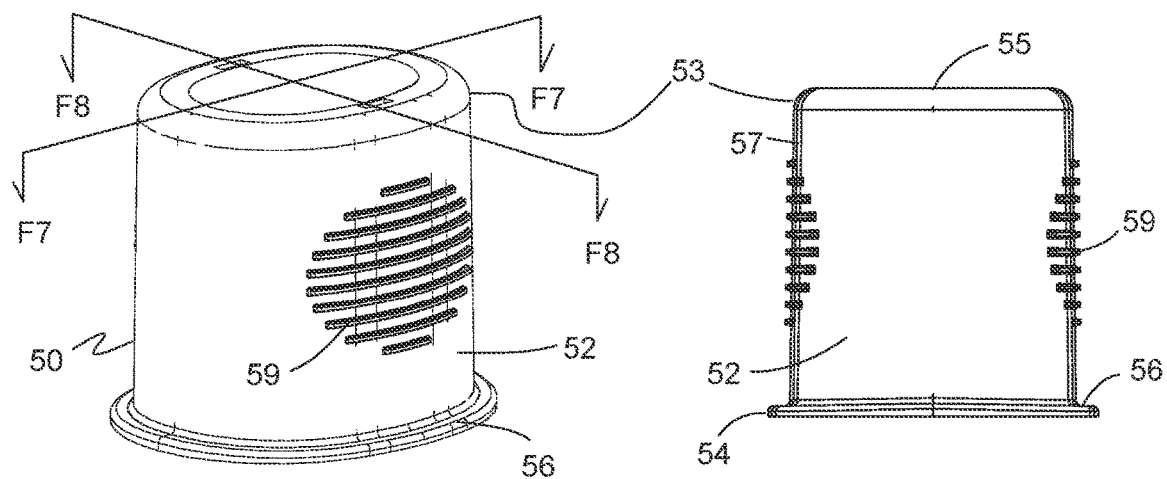
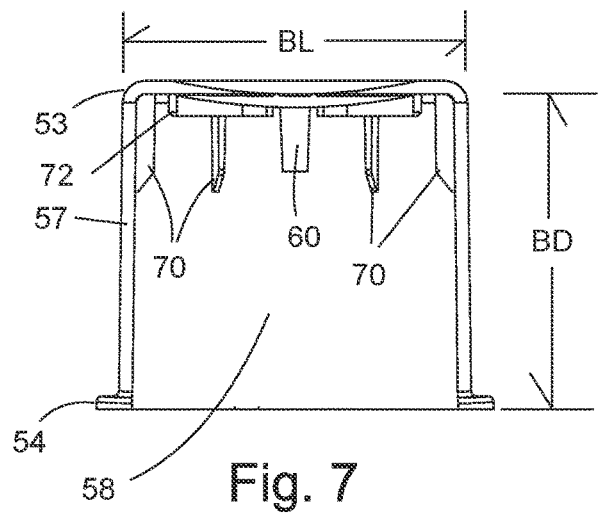
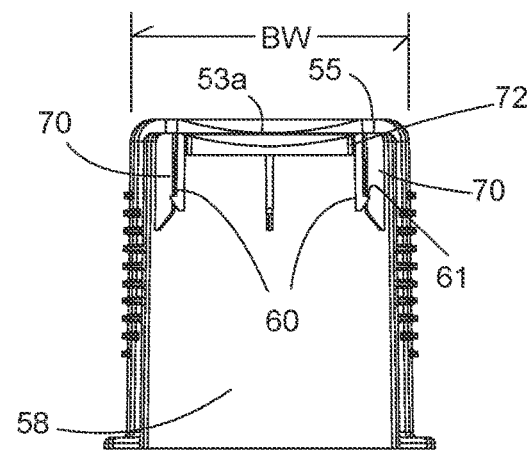
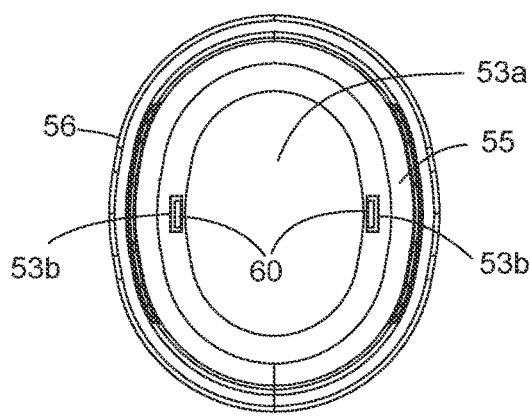
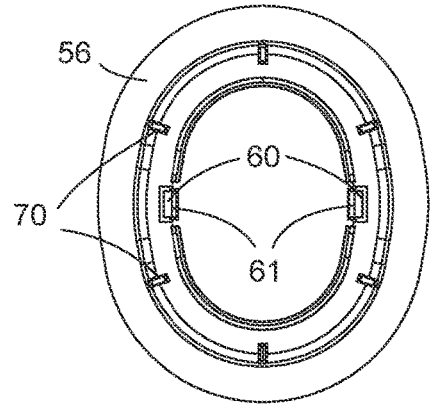
Fig. 5   Fig. 6   Fig. 7   Fig. 8   Fig. 9   Fig. 10

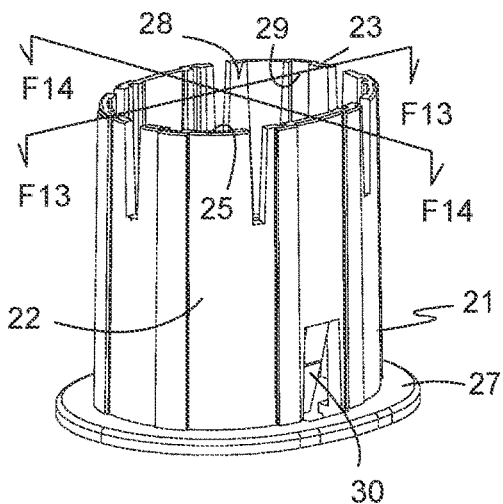
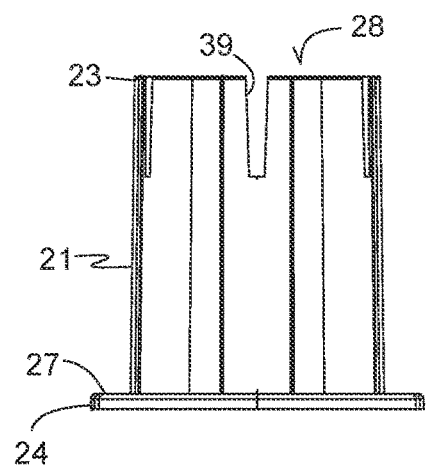
Fig. 11  Fig. 12
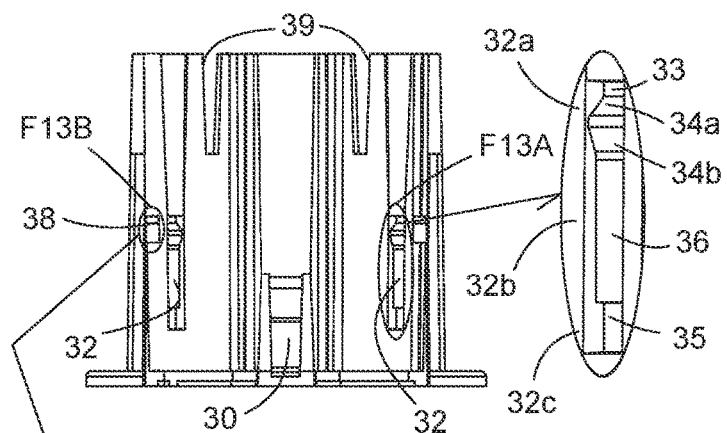
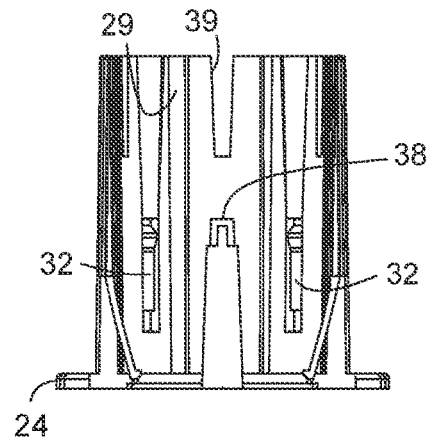
Fig. 13   Fig. 13A   Fig. 14
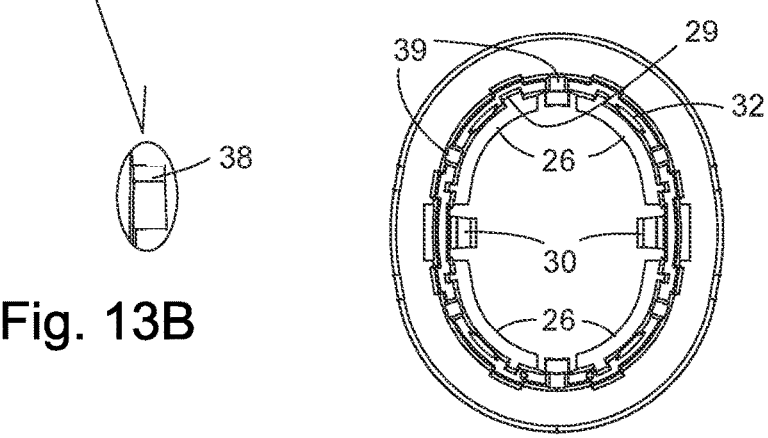
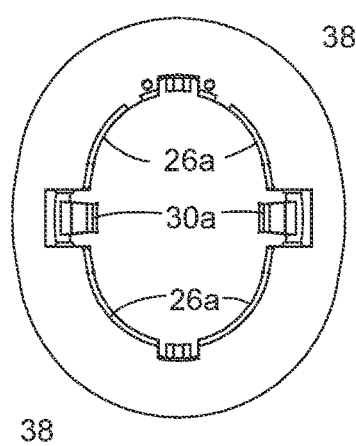
Fig. 13B
Fig. 15
Fig. 16

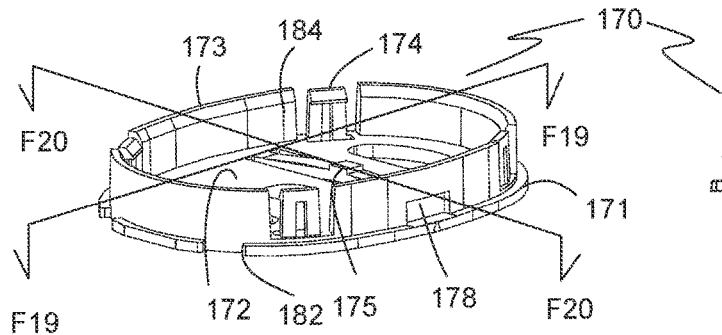
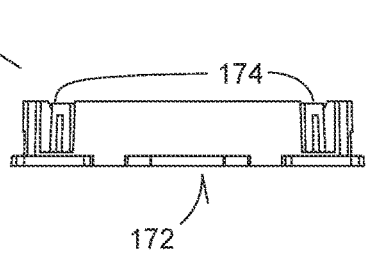
Fig. 17　　　　　　　　Fig. 18
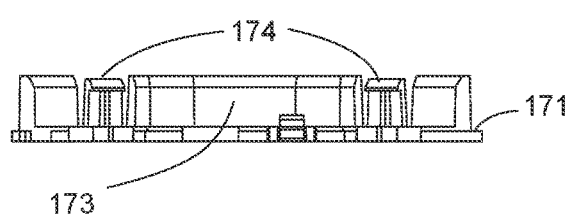
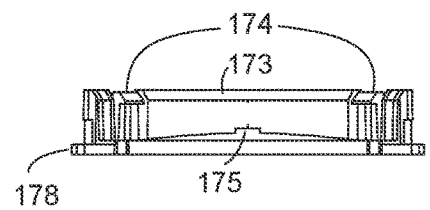
Fig. 19　　　　　　　　Fig. 20
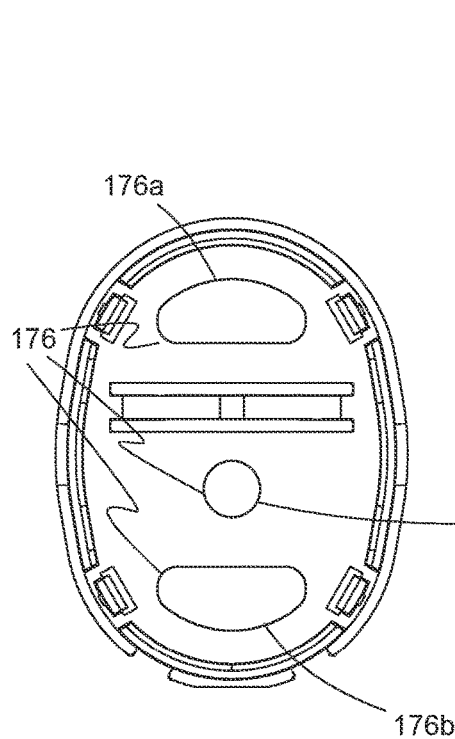
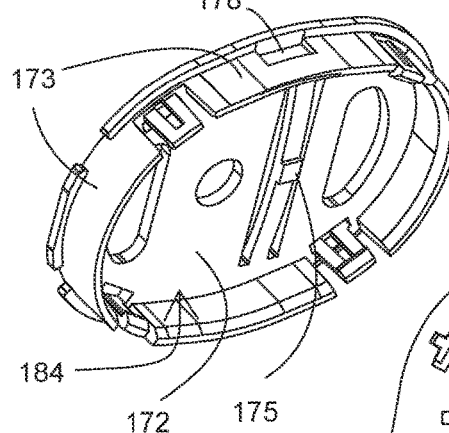
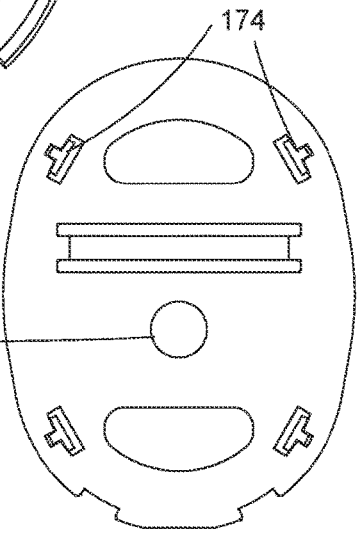
Fig. 20A
Fig. 21　　　　　　　　Fig. 22

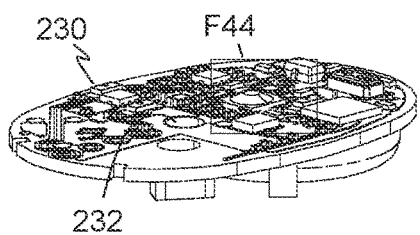 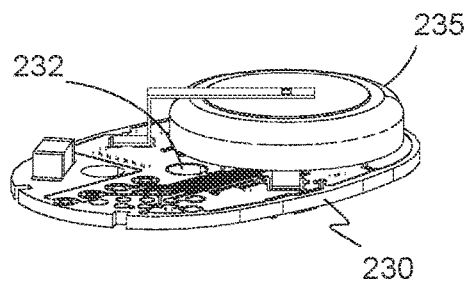
Fig. 42     Fig. 43
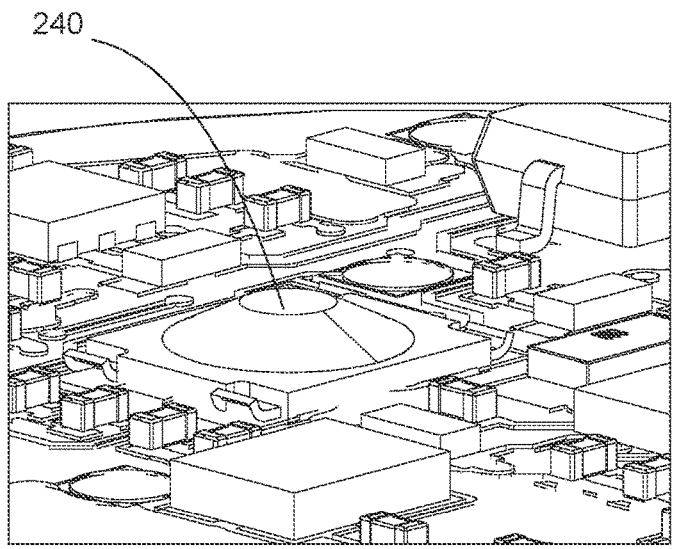
Fig. 44
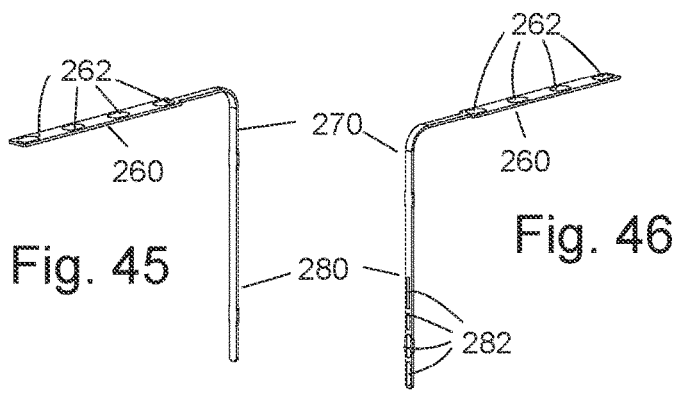 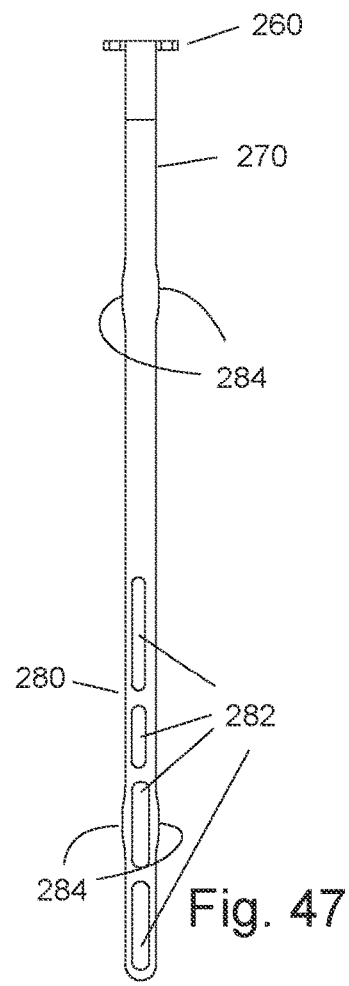
Fig. 45     Fig. 46     Fig. 47

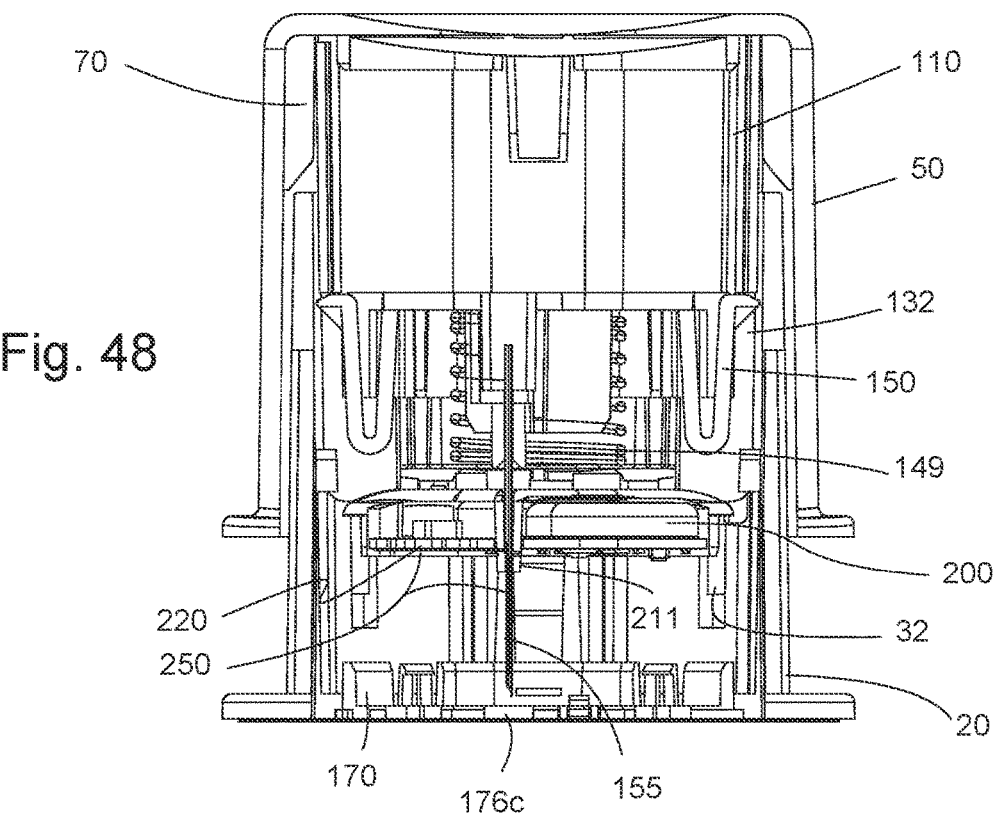
Fig. 48
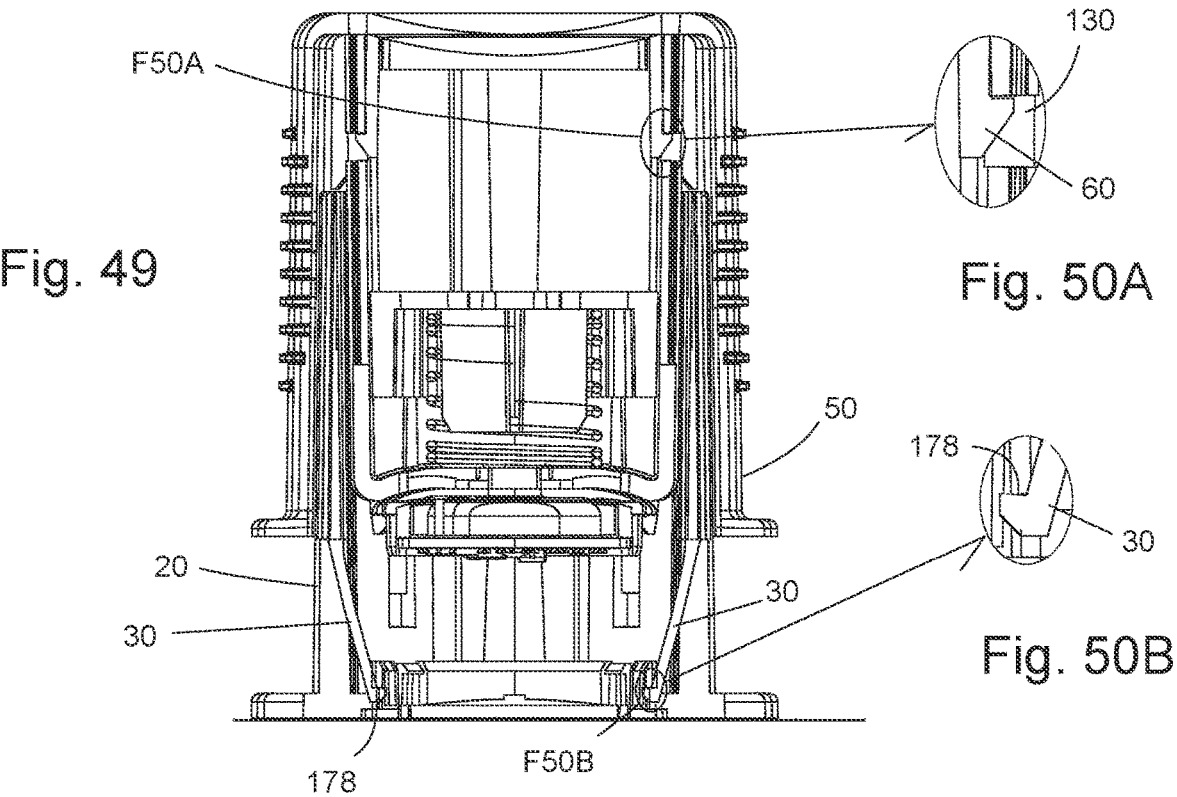
Fig. 49
Fig. 50A
Fig. 50B

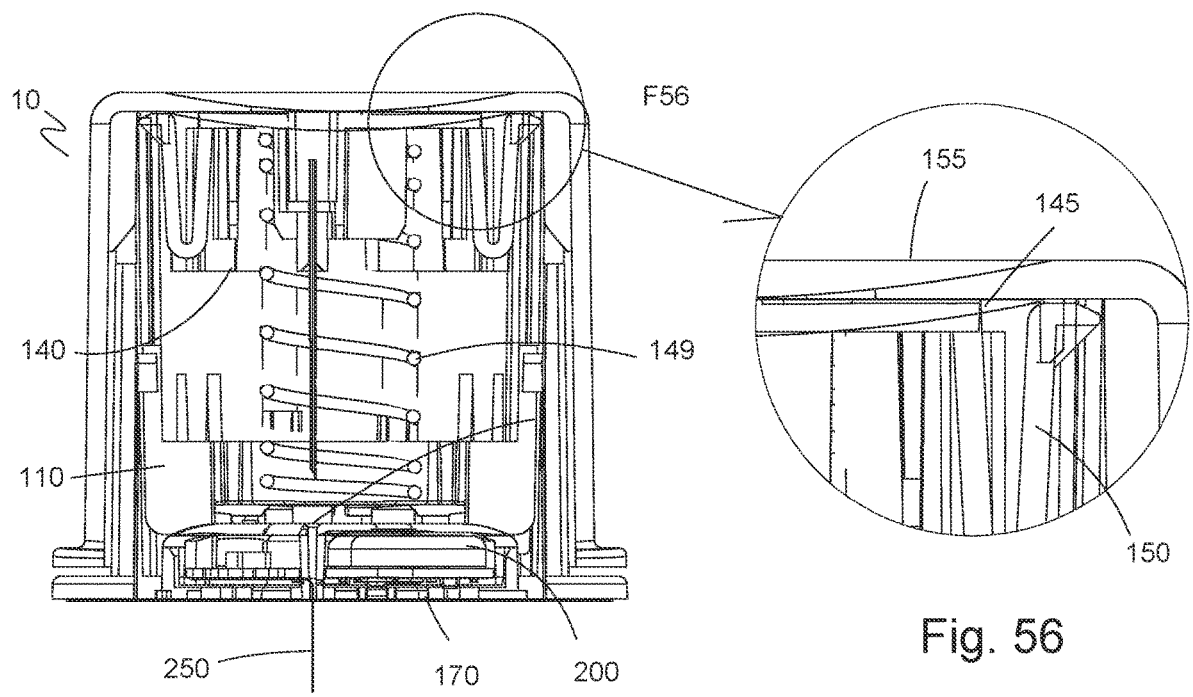
Fig. 55
Fig. 56
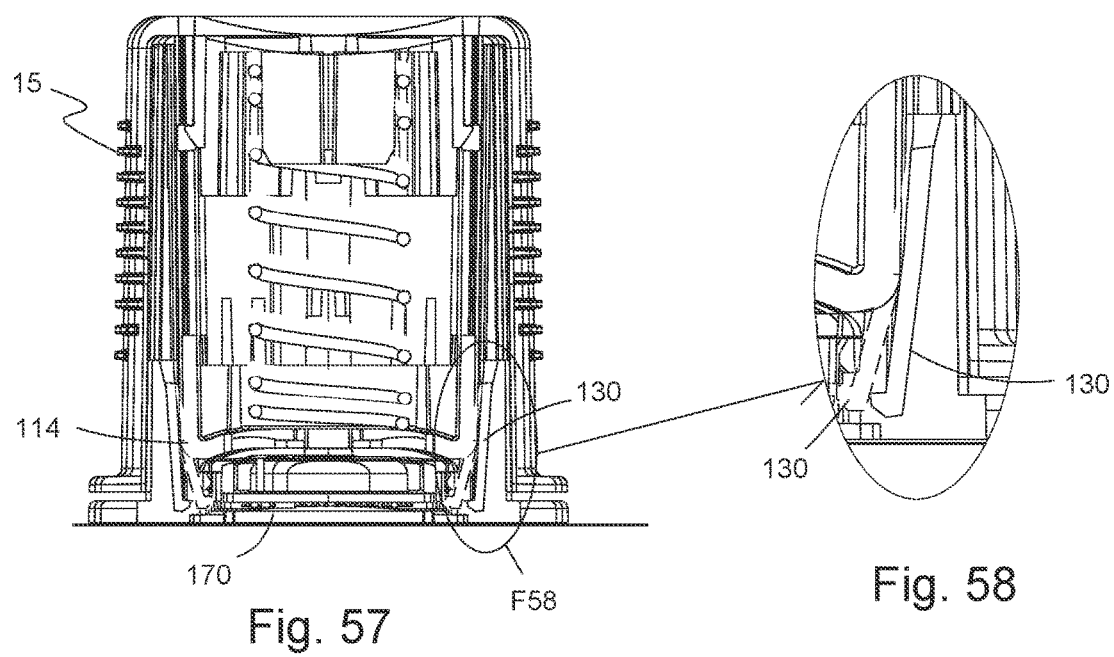
Fig. 57
Fig. 58

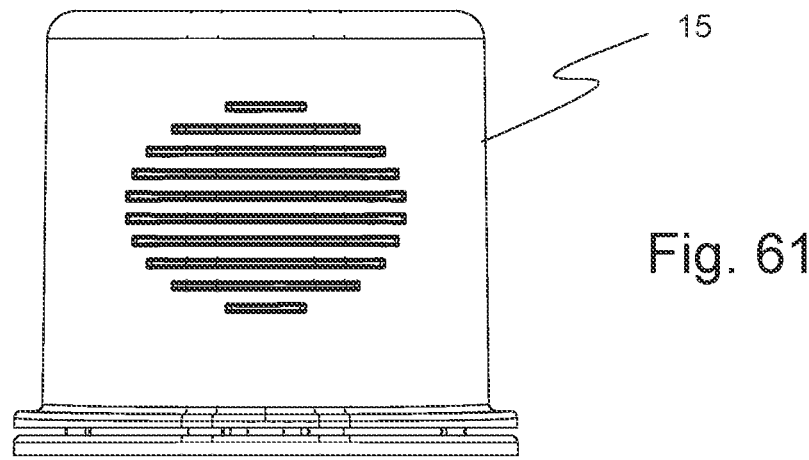
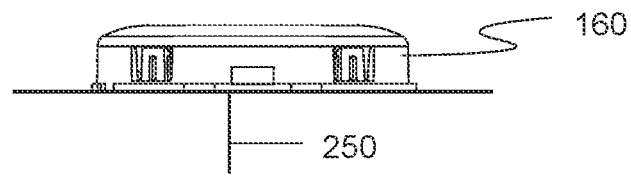
Fig. 61
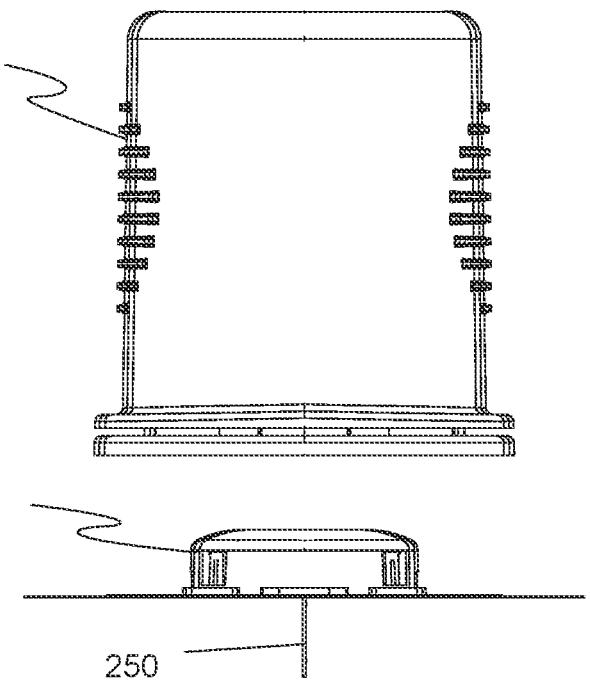
Fig. 62

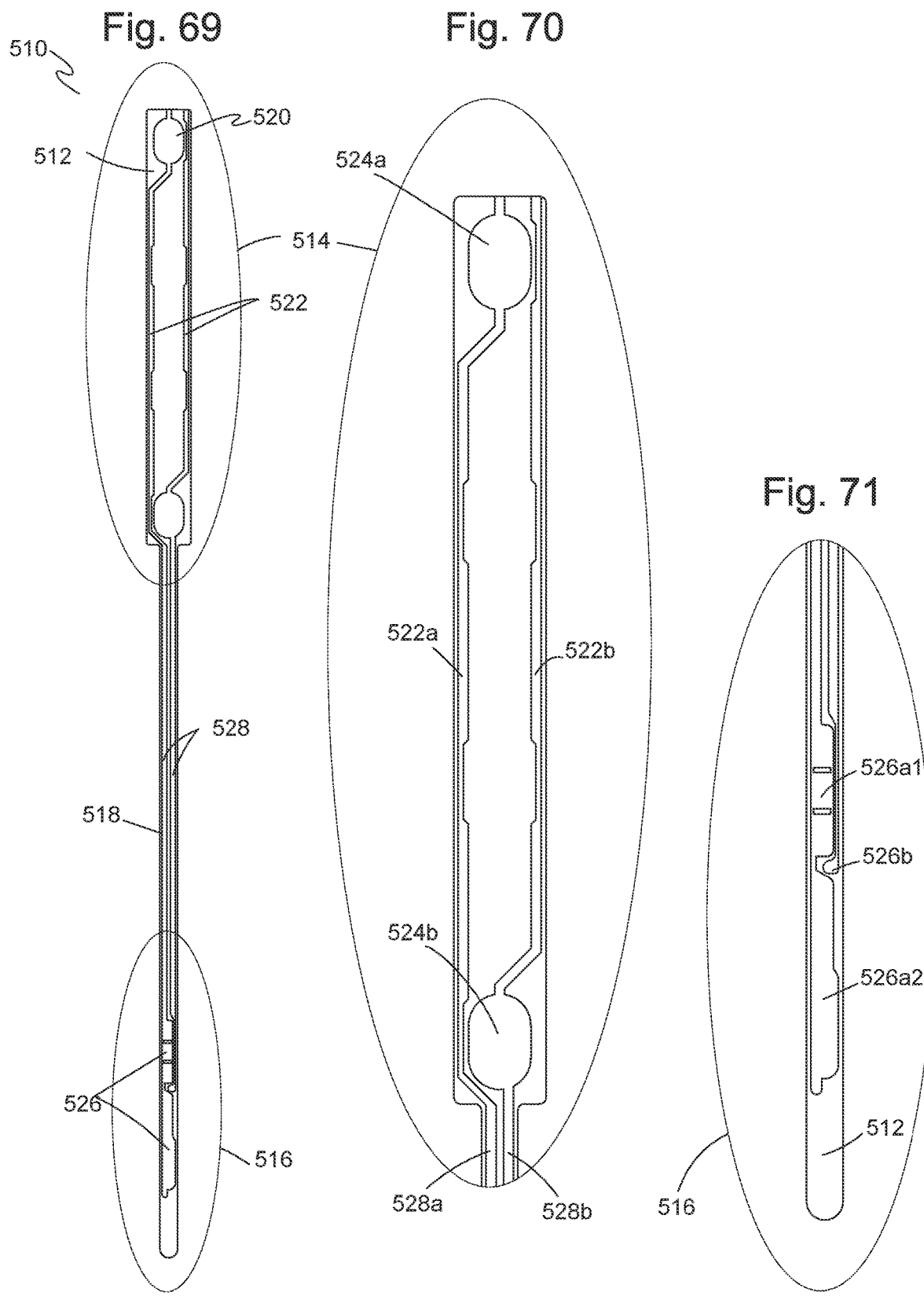

SUBCUTANEOUS ANALYTE SENSOR APPLICATOR AND CONTINUOUS MONITORING SYSTEM

Cross-Reference to Related Applications and Priority

This patent application claims priority from PCT Patent Application No. PCT/US19/32114 filed May 14, 2019, which is herein incorporated by reference in its entirety.

BACKGROUND OF THE INVENTION

1. Field of the Invention

The present invention relates generally to continuous analyte monitoring. More particularly, the present invention relates to an analyte monitoring system having a subcutaneous insertable analyte sensor, an inserter assembly and reader.

2. Description of the Prior Art

Continuous analyte monitoring devices have been developed for implanting into a patient's skin. Continuous monitoring systems typically use a tiny implantable sensor that is inserted under the skin, or into the subcutaneous fat layer to check analyte levels in the tissue fluid. A transmitter sends information about the analyte levels by way of, for example, a wire to a monitor or wirelessly by radio waves from the sensor to a wireless monitor. These devices are typically implanted for three to seven days of use to monitor in real-time a patient's glucose level.

One such device is disclosed in PCT International Application Publication No. WO 2018/118061 to Thomas H. Peterson et al. A continuous glucose monitoring system and method is disclosed and has an inserter assembly for inserting a sensor through the skin and into subcutaneous tissue where an inserter housing with the sensor remains on the skin after insertion, a sensor housing cover attachable to the sensor housing after insertion where the sensor housing cover has an electronic module and a battery, and an electronic device equipped with wireless communication for communicating with the electronic module of the sensor housing cover assembly, the electronic device configured for receiving input signals from the sensor, converting the input signals to analyte date, displaying the analyte data on a user interface of the electronic device, storing the data for recall, and creating and/or sending reports of the data.

U.S. Patent Application Publication No. 2018/0235520 to Vivek Rao et al. Systems, devices and methods are provided for inserting at least a portion of an in vivo analyte sensor, such as a dermal sensor, for sensing an analyte level in a bodily fluid of a subject. An applicator is positioned against a skin surface and a force is applied to the applicator causing at least a portion of a sharp and an in vivo analyte sensor to be positioned in the body of the subject. In particular, disclosed herein are embodiments of applicators designed to prevent premature sharp withdrawal and/or reduce the likelihood of improper sensor insertion. Also disclosed are embodiments of applicators including sharp modules having an angled sharp which can be configured to create an insertion path for a sensor.

U.S. Patent Application Publication No. 2016/0058344 to Vivek Rao et al. Systems, devices, and methods are provided for the assembly and subsequent delivery of an in vivo analyte sensor. An applicator with sensor electronics is inserted into a tray containing an assembly that includes a sharp and an analyte sensor. The insertion causes the assembly to couple with the sensor electronics and form a deliverable sensor control device retained within the applicator, which can then be placed in position on a body of a user to monitor that user's analyte levels.

U.S. Patent Application Publication No. 2016/0058344 to Thomas H. Peterson et al. The device is an apparatus for the subcutaneous implantation of in-vivo sensors. The device is an inserter assembly for continuous glucose monitoring with medication delivery capability where the assembly has a deployment button containing a needle deployment mechanism having a sharp held in a pre-release position, a housing body in which the deployment button is movably received within a top end of the housing body where the housing body has a sensor deployment assembly containing a lumen and a sensor disposed within the lumen and extending out of the lumen to a circuit board that is part of the sensor deployment assembly. The sensor deployment assembly matingly connects to the sharp where the sharp extends beyond the sensor deployment assembly and contains the sensor not fixedly attached to the sharp, and a sensor housing releasably received within a lower end of the housing body. The sharp extends into a sensor deployment assembly recess within the sensor housing and directly above a sensor opening in a bottom of the sensor housing.

U.S. Pat. No. 10,213,139 to Vivek Rao et al. discloses systems, devices, and methods for the assembly and subsequent delivery of an in vivo analyte sensor. An applicator with sensor electronics is inserted into a tray containing an assembly that includes a sharp and an analyte sensor. The insertion causes the assembly to couple with the sensor electronics and form a deliverable sensor control device retained within the applicator, which can then be placed in position on a body of a user to monitor that user's analyte levels.

U.S. Pat. No. 10,010,280 to Manuel L. Donnay et al. discloses an apparatus for insertion of a medical device in the skin of a subject is provided, as well as methods of inserting medical devices. Embodiments include removing a substantially cylindrical cap from an inserter to expose a substantially cylindrical sleeve, removing a cover from a substantially cylindrical container holding sensor components, and fitting the sensor components into the inserter.

U.S. Pat. No. 9,788,771 to Gary A. Stafford discloses an automatic sensor inserter for placing a transcutaneous sensor into the skin of a living body. According to aspects of the invention, characteristics of the insertion such as sensor insertion speed may be varied by a user. In some embodiments, insertion speed may be varied by changing an amount of drive spring compression. The amount of spring compression may be selected from a continuous range of settings and/or it may be selected from a finite number of discrete settings. Methods associated with the use of the automatic inserter are also covered.

U.S. Pat. No. 9,750,444 to Gary A. Stafford discloses systems and methods for providing a compressible interconnect for allowing electrical communication between an electronics unit and an analyte sensor in an on-body analyte monitoring device. In other embodiments, systems and methods are provided for reducing the Z-height of an on-body analyte monitoring device by utilizing novel interconnects.

U.S. Pat. No. 9,402,570 to Louis Pace et al. discloses devices associated with on-body analyte sensor units are disclosed. These devices include any of packaging and/or loading systems, applicators and elements of the on-body sensor units themselves. Also, various approaches to connecting electrochemical analyte sensors to and/or within associated on-body analyte sensor units are disclosed. The connector approaches variously involve the use of unique sensor and ancillary element arrangements to facilitate assembly of separate electronics assemblies and sensor elements that are kept apart until the end user brings them together.

U.S. Pat. No. 5,299,571 to John Mastrototaro discloses a device for implantation of in-vivo sensors. The apparatus includes a housing, a dual-lumen tube extending therefrom, and an in-vivo sensor received within one of the lumens of the tube. A needle is received within the other lumen of the tube, and is used to insert the tube through the skin. After implantation, the needle is removed, and the flexible tube and sensor remain beneath the skin.

U.S. Patent Application Publication 2010/0022863 (2010, Mogensen et al.) discloses an inserter for a transcutaneous sensor. The inserter includes a needle unit and a sensor housing. The needle unit includes a needle hub and a carrier body. The sensor housing and the needle hub are releasably connected and when they are connected, the insertion needle is placed along the sensor (e.g. surrounding the sensor wholly or partly). The carrier body guides the movement relative to the housing between a retracted and an advanced position. When released, the needle unit and the sensor housing are forced by a spring unit to an advanced position where the needle and sensor are placed subcutaneously. Upwardly-bent parts on the leg of the housing set the insertion angle of about 30° into the skin of the patient.

U.S. Patent Application Publication 2012/0226122 (2012, Meuniot et al.) discloses an inserter device for an analyte sensor. The device includes a housing that is positioned above the subcutaneous fat layer, a blade shuttle, and a sensor shuttle. A spring is compressed between the blade shuttle and the sensor shuttle. The blade shuttle and sensor shuttle move towards the subcutaneous fat layer. When a spring force is released by the spring, the blade shuttle moves towards and pierces into the subcutaneous fat layer creating a pathway into the subcutaneous fat layer. The analyte sensor is implanted by the sensor shuttle by following the blade shuttle into the pathway created by the blade shuttle. The blade shuttle is then retracted from the subcutaneous fat layer, leaving the analyte sensor in the fat layer.

U.S. Patent Application Publication 2013/0256289 (2013, Hardvary et al.) discloses a diagnostic device. The diagnostic device has partially retractable hollow guide needles for the intradermal placement of diagnostic elements fixedly connected to measuring means within this device. This obviates the need to remove the guide needle and to connect the diagnostic elements to the measuring means after placement into the skin.

SUMMARY OF THE INVENTION

In the present disclosure, the term "substantially simultaneously" means that the individual actions that occur within a subcutaneous sensor insertion applicator of the present invention when the insertion applicator is activated by a user/patient to insert a sensor subcutaneously in the skin of a patient (i.e. to assemble the sensor module as a single unit, to insert the sensor subcutaneously, to retract the needle assembly, to turn on the power switch to the electro-sensor assembly, to release the sensor module from the applicator module, and to release the applicator module from the surface of the skin) cannot be perceived by a human during the sensor insertion process.

It is an object of the present invention to provide an all-inclusive, single use, continuous analyte monitoring system.

The present invention achieves these and other objectives by providing continuous analyte monitoring system and method that includes an applicator module for inserting a sensor through the skin and into subcutaneous tissue where a sensor module remains on the skin after insertion and an electronic display device such as, for example, a smart phone and the like that is equipped with wireless communication for communicating with the sensor module, the electronic display device configured for receiving input signals from the sensor, converting the input signals to analyte data, displaying the analyte data on a user interface of the electronic device, storing the data for recall, and creating and/or sending reports of the data. Various sensors, needles and electronic display devices are disclosed in PCT Patent Application Publication No. WO 2018/118061 to Thomas H. Peterson et al., which publication is herein incorporated by reference in its entirety.

In one embodiment, there is disclosed an all-inclusive, single-use, subcutaneous analyte sensor applicator and monitoring system. The system includes an inserter module and a sensor module. The inserter module includes an applicator housing, a deployment button where the applicator housing is partially received within a button chamber, and a pre-loaded insertion assembly completely disposed and secured within the button chamber and partially disposed within the applicator housing chamber when the deployment button is in an initial, loaded position. The pre-loaded insertion assembly includes an assembly housing, a biasing element disposed within an assembly housing chamber, and a needle assembly disposed within the assembly housing chamber where the biasing element is in a compressed state between the needle assembly and an assembly housing bottom. The sensor module includes a sensor lower housing releasably connected to the applicator housing, a sensor upper housing removably retained against the insertion assembly housing and spaced from the sensor lower housing, and an electro-sensor assembly disposed within the sensor upper housing where (a) the electro-sensor assembly has an electronic circuit with a power switch and a sensor electrically coupled to the electronic circuit and (b) where the sensor is temporarily disposed within a needle of the needle assembly when the applicator system is in the initial pre-loaded position.

In another aspect of the invention, the applicator housing has an applicator elongated body defining the applicator housing chamber, a proximal internal body flange portion and an applicator housing retaining arm adjacent a proximal applicator housing end.

In another embodiment, the deployment button has a button elongated body defining the button chamber, a closed button distal end and a button retaining arm extends within the button chamber from the closed button distal end toward an open button proximal end a predefined distance.

In one embodiment, the assembly housing has an assembly housing body having an assembly circumferential wall defining the assembly housing chamber, a closed housing proximal end, a recessed housing bottom at the closed housing proximal end, an open housing distal end, an assembly housing retaining arm formed in the assembly circumferential wall and extending toward the closed housing proximal end, a plurality of housing retaining fingers formed in the assembly circumferential wall and extending toward and beyond the closed housing proximal end and having an inward-facing housing finger hook surface, an assembly housing locking slot that interacts with the button retaining arm to secure the pre-loaded insertion assembly within the button chamber, and a needle assembly locking slot that interacts with the needle body retaining arm.

In one embodiment, the biasing element is positioned on one end against a recessed housing bottom of the assembly housing.

In one embodiment, the needle assembly has a needle body with a needle body circumferential wall, a closed needle body distal end forming a needle body top, an open needle body proximal end where the needle body retaining arm is formed in the needle body circumferential wall to thereby position an outward-facing needle retaining arm hook surface adjacent to the closed needle body distal end, and a needle receiving portion formed in the needle body top where a needle is secured adjacent a needle distal end and extends parallel to the needle body circumferential wall a predefined distance beyond the open needle body proximal end and where the biasing element is positioned against the closed needle body distal end through the open needle body proximal end. The outward-facing needle is offset from a central axis of the insertion applicator.

In one embodiment, the sensor lower housing has a plurality of lower housing locking elements extending upward a predefined distance from a lower housing bottom into the applicator housing chamber.

In one embodiment, the sensor lower housing has a lower housing locking recess in a lower housing wall where the applicator housing retaining arm engages the lower housing locking recess when the deployment button is in the initial pre-loaded position.

In one embodiment, the sensor upper housing has an upper housing circumferential wall extending from the upper housing top forming a housing top flange portion in a perimeter of the upper housing top. The upper housing circumferential wall has a plurality of upper housing locking recesses adapted for mating connection to a plurality of locking elements of the sensor lower housing.

In one embodiment, the electro-sensor assembly includes a power source coupled between the electronic circuit and the power switch.

In another embodiment of the inserter assembly, the bottom surface of the sensor housing is configured to adhere to the patient during implantation of the sensor. In one embodiment, for example, the sensor deployment locking mechanism includes one or more bores with a resilient deployment catch extending upward from an inside bottom surface of the sensor housing, where the resilient deployment catch is biased to engage a deployment catch surface of the one or more bores in the sensor deployment assembly.

In another embodiment of the inserter assembly, the sensor, when implanted subcutaneously in the patient, has a working electrode of an electrode system on the sensor extending into the patient by about 4 mm to about 7 mm. In another embodiment, the sensor, when implanted subcutaneously in the patient, has a working electrode of an electrode system on the sensor extending into the patient by about 2 mm to about 10 mm.

Another aspect of the present invention is directed to a multi-layer, thin-film substrate assembly for use in forming a subcutaneous analyte sensor. In one embodiment, the substrate assembly has a base layer made of an electrically-insulating material, where the base layer has a base layer substrate with a base layer proximal end portion, a base layer distal end portion, and a base layer middle portion extending longitudinally between the base layer proximal end portion and the base layer distal end portion.

A first metallized layer is disposed on the base layer substrate and defines at least one circuit extending longitudinally along the base layer substrate. Each circuit has an electrically-conductive contact pad formed at each of the base layer proximal end portion and the base layer distal end portion with an electrically-conductive trace electrically coupling the electrically-conductive contact pad at the base layer proximal end portion with the electrically-conductive pad at the base layer distal end portion.

A middle layer is disposed over the base layer, where the middle layer has a middle layer substrate made of an electrically-insulating material with a second proximal end portion, a second distal end portion, and a second middle portion. The middle layer is aligned with the base layer and has a plurality of middle layer through openings with side walls. Each of the middle layer through openings is in communication with a respective one of the electrically-conductive contact pad of the circuit(s) of the base layer.

A second metallized layer is disposed on the middle layer and the side walls of the through openings. The second metallized layer defines at least two circuits, where each of the circuits of the second metallized layer has an electrically-conductive contact pad formed at the second proximal end portion and at the second distal end portion with an electrically-conductive trace electrically coupling the electrically-conductive contact pad at the middle layer second proximal end portion with the electrically-conductive pad at the middle layer distal end portion. One of the circuits is electrically coupled to the circuit(s) of the base layer by way of the plurality of middle layer through openings.

A top layer made of an electrically-insulating material is disposed over the middle layer. The top layer has a plurality of contact openings that coincide with each electrically-conductive contact pad of the middle layer proximal end portion and a plurality of sensor openings that coincide with each electrically-conductive contact pad of the middle layer distal end portion, thereby creating a substrate assembly with an substrate proximal end portion, an substrate distal end portion and an assembly middle portion extending longitudinally between the substrate proximal end portion and the substrate distal end portion. Each electrically-conductive contact pad at the second distal end portion is adapted to receive an electrode reagent to form a respective electrode and each electrically-conductive contact pad at the second proximal end portion is adapted to receive an electrical contact.

In another embodiment, the multi-layer, thin-film substrate assembly has multiple middle layers.

In another embodiment, the base layer, the circuit(s) of the first metallized layer, the middle layer, the middle layer circuits, and the top layer together impart an arcuate shape to the substrate assembly from the substrate proximal end portion to the substrate distal end portion.

In another embodiment of the substrate assembly, the electrically insulating material of each of the base layer, the middle layer, and the top layer is polyimide that is spun-formed and thermally cured.

In one embodiment of the substrate assembly, for example, the base layer and the middle layer have a thickness of about 10 microns. In another embodiment of the substrate assembly, the top layer has a thickness about five times the thickness of the middle layer. In another embodiment of the substrate assembly, the top layer has a thickness of about 55 microns. In another embodiment of the substrate assembly, the sensor assembly has a thickness of about 75 microns. In yet another embodiment, each of the substrate distal end portion and the assembly middle portion has a width of about 279 microns.

In another embodiment of the substrate assembly, the first metallized layer has a thickness in the range of about 900 Angstroms to about 1,500 Angstroms.

In another embodiment of the substrate assembly, the first metallized layer and the second metallized layer each includes gold. In another embodiment, the first metallized layer and the second metallized layer each includes a layer of chromium disposed against the base layer substrate and the middle layer substrate, respectively, and a layer of gold disposed on top of the layer of chromium. In another embodiment, the second metallized layer includes a layer of chromium disposed against the middle layer substrate, a layer of gold disposed on top of the layer of chromium, and a layer of platinum disposed on top of the layer of gold.

In another embodiment of the substrate assembly, the base layer has at least two circuits with respective electrically-conductive pads for each circuit at the base layer proximal end portion and the base layer distal end portion. The middle layer has at least two second-layer circuits with electrically-conductive pads for each second-layer circuit at the middle layer proximal end portion and the middle layer distal end portion. In one embodiment, for example, the first metallized layer of the base layer includes at least two additional electrically-conductive contact pads at the base layer distal end portion that aligns and coincides with the electrically-conductive pads at the middle layer distal end portion.

Another aspect of the present invention is directed to an electrochemical sensor assembly for use as a subcutaneous analyte sensor. In one embodiment, the electrode assembly has a base layer with a base layer substrate of electrically-insulating material that defines a base layer proximal end portion, a base layer distal end portion, and a base layer middle portion between the base layer proximal end portion and the base layer distal end portion. The base layer also has a first metallized layer disposed on the base layer substrate and defining at least one circuit extending longitudinally along the base layer substrate. Each circuit has an electrically-conductive contact pad formed at each of the base layer proximal end portion and the base layer distal end portion. An electrically-conductive trace electrically couples the electrically-conductive contact pad at the base layer proximal end portion with the electrically-conductive pad at the base layer distal end portion.

A middle layer is disposed over the base layer and has a middle layer substrate of electrically-insulating material. The middle layer substrate has a middle layer proximal end portion, a middle layer distal end portion, and a middle layer middle portion, where the middle layer is aligned with the base layer and has a plurality of second-layer through openings with side walls. Each of the plurality of second-layer through openings is in communication with a respective one of the electrically-conductive contact pad of the at least one circuit of the base layer. A second metallized layer is disposed on the middle layer substrate and the side walls of the second-layer through openings. The second metallized layer defines at least two circuits, where each of the second-layer circuits has an electrically-conductive contact pad formed at each of the middle layer proximal end portion and the middle layer distal end portion with an electrically-conductive trace electrically coupling the electrically-conductive contact pad at the middle layer proximal end portion with the electrically-conductive pad at the middle layer distal end portion. One of the at least two second-layer circuits is electrically coupled to the at least one circuit of the base layer by way of the plurality of second-layer through openings.

A top layer of electrically-insulating material is disposed over the middle layer. The top layer has a plurality of contact openings that coincide with each electrically-conductive contact pad of the middle layer proximal end portion and a plurality of sensor wells that coincide with each of the electrically-conductive contact pad of the middle layer distal end portion, thereby creating a substrate assembly with an substrate proximal end portion, an substrate distal end portion and an assembly middle portion extending longitudinally between the substrate proximal end portion and the substrate distal end portion.

A sensing layer is disposed on at least one electrically-conductive contact pad formed at the middle layer distal end portion to form at least a first working electrode. A reference layer is disposed on at least one electrically-conductive contact pad formed at the middle layer distal end portion forming a reference electrode. In another embodiment, there is further included a counter electrode and at least a second working electrode (also called a blank electrode because it is used to measure background current caused by interferents in the sample and not to measure a specific analyte). In still other embodiments, there are one or more additional working electrodes adapted to measure other specific analytes. In one embodiment, the at least first working electrode is a glucose measuring electrode.

In one embodiment, sensing layer includes three coating layers. A base coating later disposed directly on the metallized pad use to form a working electrode that contains PHEMA and glucose oxidase and/or glucose dehydrogenase, a second coating layer disposed directly on the base coating layer that contains PHEMA and a plurality of microspheres made of a material having substantially no or little permeability to glucose but a substantially high permeability to oxygen, and a third coating layer over the second coating layer, the third coating layer containing PHEMA and a material that prevents release of hydrogen peroxide from the sensing layer. In one embodiment, the microspheres are made from polydimethylsiloxane. In one embodiment, the third coating layer contains catalase.

In another embodiment, the base coating layer contains PHEMA, glucose oxidase and/or glucose dehydrogenase and a quantity of microspheres that is less that the quantity of microspheres in the second coating layer.

In another embodiment of the electrochemical sensor assembly, the base layer, the at least one circuit, the middle layer, the at least second-layer one circuit, and the top layer together impart an arcuate shape to the substrate assembly from the substrate proximal end portion to the substrate distal end portion.

In another embodiment of the electrochemical sensor assembly, each of the base layer substrate, the middle layer substrate, and the top layer substrate are polyimide that is spun-formed and thermally cured.

In another embodiment of the electrochemical sensor assembly, the base layer substrate and the middle layer substrate each have a thickness of about 10 microns. In another embodiment, the top layer has a thickness about five times the thickness of the middle layer substrate. In another embodiment, the top layer has a thickness of about 55 microns. In another embodiment, the sensor assembly has a thickness of about 75 microns. In another embodiment, each of the substrate distal end portion and the assembly middle portion has a width of about 279 microns.

In another embodiment of the electrochemical sensor assembly, the first metallized layer has a thickness in the range of about 900 Angstroms to about 1,500 Angstroms. In one embodiment, the first metallized layer and the second metallized layer each includes gold. In another embodiment, the first metallized layer and the second metallized layer each includes a layer of chromium disposed against the base layer substrate and the middle layer substrate, respectively, and a layer of gold disposed on top of the layer of chromium.

In another embodiment of the electrochemical sensor assembly, the second metallized layer includes a layer of chromium disposed against the middle layer substrate, a layer of gold disposed on top of the layer of chromium, and a layer of platinum disposed on top of the layer of gold.

In another embodiment of the electrochemical sensor assembly, the base layer includes at least two circuits, where one electrically-conductive pad with the sensing layer at the middle layer distal end portion forms a working electrode circuit, and where a second electrically-conductive pad at the middle layer distal end portion forms a blank electrode.

In another embodiment of the electrochemical sensor assembly, the base layer has at least two circuits and the middle layer has at least 2 circuits with respective electrically-conductive pads for each circuit at the respective distal end portion and the proximal end portion. In another embodiment, the first metallized layer of the base layer includes at least two additional electrically-conductive contact pads at the base layer distal end portion that align and coincide with the electrically-conductive pads at the middle layer distal end portion.

In another embodiment of the present invention, there is discloses a continuous glucose monitoring system. The system has an inserter assembly, a sensor housing cover assembly, and an electronic device. The inserter assembly has an inserter housing, a deployment button disposed within the inserter housing such that the deployment button is slidable from a first position to a second position only for deployment of a subcutaneous sensor into subcutaneous tissue through the skin, and a sensor housing for receiving and capturing a sensor deployment assembly from the deployment button where the sensor deployment assembly has a subcutaneous sensor. The sensor housing cover assembly configured for attachment to the sensor housing after insertion of the subcutaneous sensor where the cover assembly has an electronic module positioned for electronic coupling to the subcutaneous sensor and capable of storing and transmitting calculated data based on the input signals from the sensor. The electronic device is equipped with wireless communication for communicating with the electronic module of the sensor housing cover assembly. The electronic device having electronic circuits and software for receiving input signals from the sensor, converting the input signals to analyte data, displaying the analyte data on a user interface of the electronic device, storing the data for recall, and creating and/or sending reports of the data.

In another embodiment, the sensor of the continuous glucose monitoring system has a base layer with a base electrical circuit, a middle layer with middle electrical circuit where the middle layer has openings to the base layer electrically connecting portions of the middle electrical circuit with portions of the base electrical circuit.

In another embodiment, a method of inserting a sensor subcutaneously is disclosed. The method includes providing an all-inclusive, single-use, subcutaneous analyte sensor applicator and monitoring system containing an inserter module coupled with a sensor module where the system is preassembled, pre-loaded and ready to use because no assembly of any portion of the system is required by the user before placement of the system on the skin of a patient and no other manipulation of the system is required by the user to power an electronic circuit within the sensor module either before or after activation of the system and insertion of the sensor subcutaneously, placing the system against a skin of a patient, and actuating the inserter assembly where the actuating step causes the applicator system to perform the following at substantially the same time: to assemble the sensor module as a single unit, to insert the sensor subcutaneously, to retract the needle assembly, to turn on the power switch to the electro-sensor assembly, to release the sensor module from the applicator module, and to release the applicator module from the surface of the skin automatically. assembling of the sensor module as a single unit against the skin of the patient, implanting the sensor subcutaneously, automatically powering the electronic circuit, and automatically separating the inserter module from the assembled sensor module.

In one embodiment, the providing step includes removing an adhesive tape cover from a bottom of the applicator housing before the placing step.

In one embodiment, the actuating step includes pushing a deployment button from an initial loaded position on an applicator housing toward the skin of the animal such that a needle containing a sensor penetrates the skin and inserts the sensor leaving the sensor deployed while the needle completely retracts into an assembly housing located within the deployment button while the deployment button locks into a second position on the application housing and the applicator housing separates from the lower sensor housing.

In another embodiment, the providing step includes attaching a double-sided adhesive pad having a pad opening to an open proximal body end of an applicator housing of the inserter module before the placing step such that the pad opening of the adhesive pad is aligned with a needle axis of the needle.

In another embodiment, a method of making an all-inclusive, single-use, subcutaneous analyte sensor applicator and monitoring system is disclosed. The method includes forming each of the following: (a) an applicator housing defining an applicator housing chamber and an applicator housing retaining arm, (b) a deployment button defining a button chamber and a button retaining arm, (c) an assembly housing defining an assembly housing chamber, an assembly housing retaining arm formed in the assembly housing and having an outward-facing housing arm hook surface, (d) a biasing element, (e) a needle assembly having a needle body and a needle fixedly attached to the needle body where the needle extends a predefined distance beyond the needle body defining a needle axis, (f) a sensor lower housing having a power actuator and a lower housing opening adapted for receiving the needle, (g) a sensor upper housing having an upper housing top with a housing top opening, and (h) an electro-sensor assembly having an electronic circuit with a power switch and a sensor electrically coupled to the electronic circuit, followed by disposing the biasing element within the assembly housing chamber of the assembly housing, inserting the needle assembly within the assembly housing chamber so that the needle body contacts the biasing element and then pushing the needle body into the assembly housing chamber to compress the biasing element until a needle body retaining arm locks into a needle assembly locking slot of the assembly housing such that the needle extends beyond a closed housing proximal end and through a housing proximal end opening, inserting the combined needle assembly, the biasing element and the assembly housing into the button chamber of the deployment button until the button retaining arm of the deployment button locks into an assembly housing locking slot of the assembly housing, attaching the sensor upper housing to the assembly housing containing the needle assembly and the biasing element such that a needle of the needle assembly extends through an upper housing top opening of the sensor upper housing, inserting the electro-sensor assembly into the sensor upper housing such that the sensor is positioned within the needle where the assembly housing, the biasing element, the needle assembly, the sensor upper housing, and the electro-sensor assembly form a pre-loaded insertion assembly, attaching the sensor lower housing to an open proximal body end of the applicator housing, and inserting a portion of the applicator housing into the button chamber a predefined distance such that an applicator body circumferential wall at an open distal body end of the applicator housing slides between the assembly housing and the deployment button until an assembly housing retaining arm catches into a distal applicator housing notch in applicator body circumferential wall.

In one embodiment, the method further includes attaching a double-sided adhesive pad having a pad opening to the open proximal body end of applicator housing such that the pad opening of the adhesive pad is aligned with the needle axis and the adhesive material facing the bottom of the applicator housing only covers and attaches to the sensor lower housing and not to the applicator housing.

BRIEF DESCRIPTION OF THE DRAWINGS

FIG. 5 is a front perspective view of one embodiment of a deployment button of the applicator.

FIG. 6 is a front plan view of the deployment button of FIG. 5.

FIG. 7 is a cross-sectional view of the deployment button of FIG. 5 taken along line F7-F7.

FIG. 8 is a cross-sectional view of the deployment button of FIG. 5 taken along line F8-F8.

FIG. 9 is a top view of the deployment button of FIG. 5.

FIG. 10 is a bottom view of the deployment button of FIG. 5.

FIG. 11 is a front perspective view of one embodiment of an applicator housing of the applicator in FIG. 4.

FIG. 12 is a front plan view of the applicator housing of FIG. 11.

FIG. 13 is a cross-sectional view of the applicator housing of FIG. 11 taken along line F13-F13.

FIG. 13A is an enlarged view of one embodiment of a cam wall surface of FIG. 13.

FIG. 13B is an enlarged view of the needle assembly housing stop 38 of FIG. 13

FIG. 14 is a cross-sectional view of the applicator housing of FIG. 11 taken along line F14-F14.

FIG. 15 is a top view of the applicator housing of FIG. 11.

FIG. 16 is a bottom view of the applicator housing of FIG. 11.

FIG. 17 is a front perspective view of one embodiment of a sensor lower housing of the applicator in FIG. 4.

FIG. 18 is a front plan view of the sensor lower housing of FIG. 17.

FIG. 19 is a cross-sectional view of the sensor lower housing of FIG. 17 taken along line F19-F19.

FIG. 20 is a cross-sectional view of the sensor lower housing of FIG. 17 taken along line F20-F20.

FIG. 20A is an angled perspective view of the inside bottom of the sensor lower housing showing one embodiment of the power activator shown in FIG. 20.

FIG. 21 is a top view of the sensor lower housing of FIG. 17.

FIG. 22 is a bottom view of the sensor lower housing of FIG. 17.

FIG. 42 is a rear, perspective, bottom view of one embodiment of the electronic circuit of the electro-sensor assembly shown in FIG. 37.

FIG. 43 is a front, perspective, top view of the electronic circuit shown in FIG. 42.

FIG. 44 is an enlarged, perspective, bottom view of the electronic circuit of FIG. 42 in the area delineates as F44 showing a power switch.

FIG. 45 is a rear, perspective view of one embodiment of a sensor of the electro-sensor assembly.

FIG. 46 is a front, perspective view of the sensor of FIG. 45.

FIG. 47 is an enlarged, front view of the sensor of FIG. 46.

FIG. 48 is a left-side, cross-sectional view of the applicator system of FIG. 1 taken along line F48-F48 in FIG. 1 showing the applicator system is a ready-to-use state.

FIG. 49 is a front, cross-sectional view of the applicator system of FIG. 1 taken along line F49-F49 in FIG. 1.

FIG. 50A is an enlarged view of the applicator system of FIG. 49 within an area delineated as F50A showing an outward-facing button retaining arm engaged in an insertion assembly housing locking slot.

FIG. 50B is an enlarged view of the applicator system of FIG. 49 within the area delineated as F50B.

FIG. 55 is a left-side, cross-sectional view of the applicator system of FIG. 48 showing the applicator system fully deployed with the needle assembly retracted within the insertion assembly housing.

FIG. 56 is an enlarged, cross-sectional view of the applicator system of FIG. 55 within an area delineated F56 showing the needle body against the closed button distal end.

FIG. 57 is a front, cross-sectional view of the applicator system of FIG. 55 fully deployed.

FIG. 58 is an enlarged, cross-sectional view of the applicator system of FIG. 57 within an area delineated as F58 showing the inward-facing applicator housing retaining arm fully released from the sensor lower housing locking recess.

FIG. 61 is right-side plan view of the fully deployed sensor applicator system showing the sensor module deployed and separated from the applicator module.

FIG. 62 is a front plan view of the fully deployed sensor applicator of FIG. 61.

FIG. 69 is a plan view of the sensor of FIG. 67 showing the base layer only with an electrical contact portion and a sensor end portion circled.

FIG. 70 is an enlarged view of the electrical contact portion of FIG. 69.

FIG. 71 is an enlarged view of the sensor end portion of FIG. 69.

DETAILED DESCRIPTION OF THE INVENTION

This disclosure is not limited to the particular embodiment(s) described herein, which embodiments may vary, and the terminology used to describe these particular embodiments is not intended to be limiting.

Figure 1:
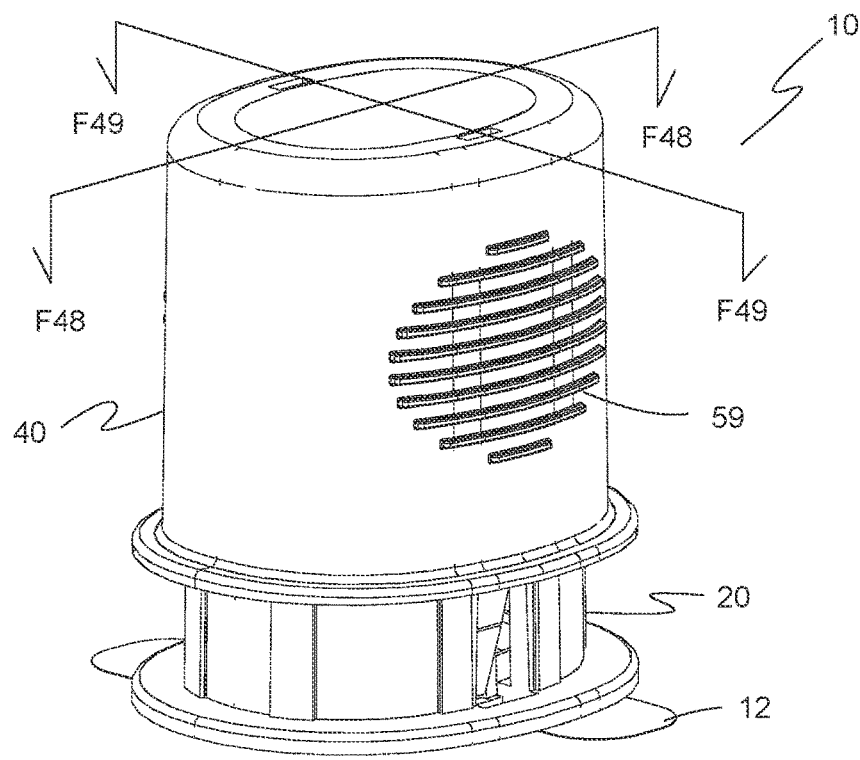
FIG. 1 is a front perspective view of one embodiment of the present invention showing a ready-to-use subcutaneous sensor applicator.
Figure 2:
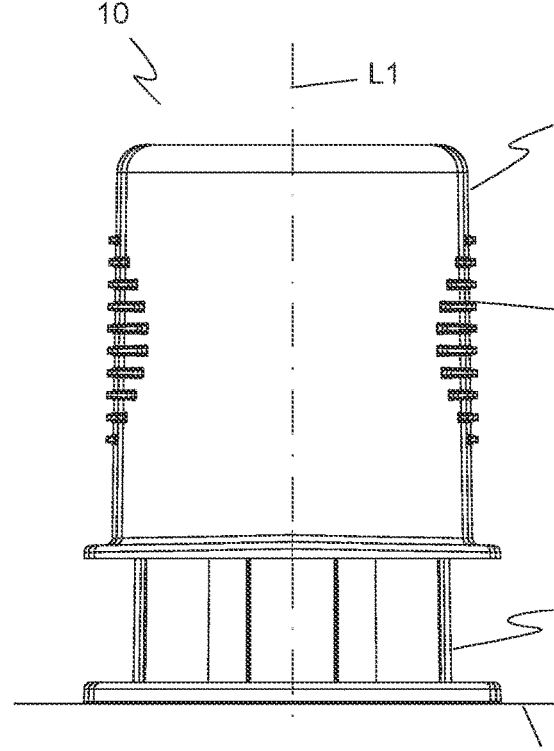
FIG. 2 is a front plan view of the applicator of FIG. 1.
Figure 3:
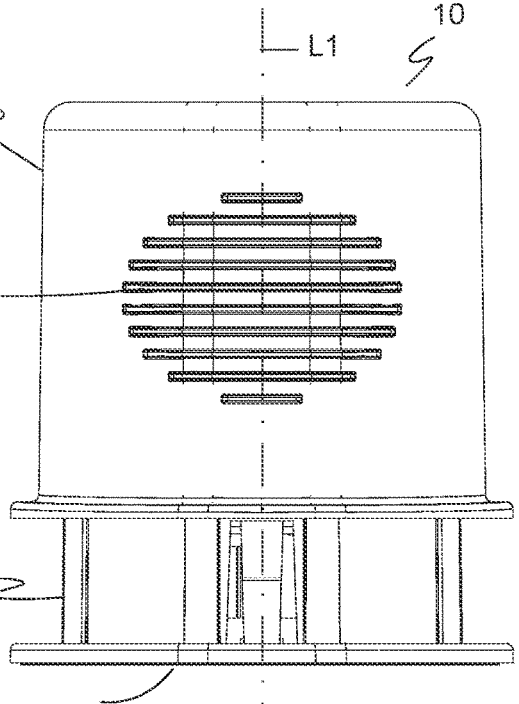
FIG. 3 is a left side plan view of the applicator of FIG. 1.
Figure 1B:
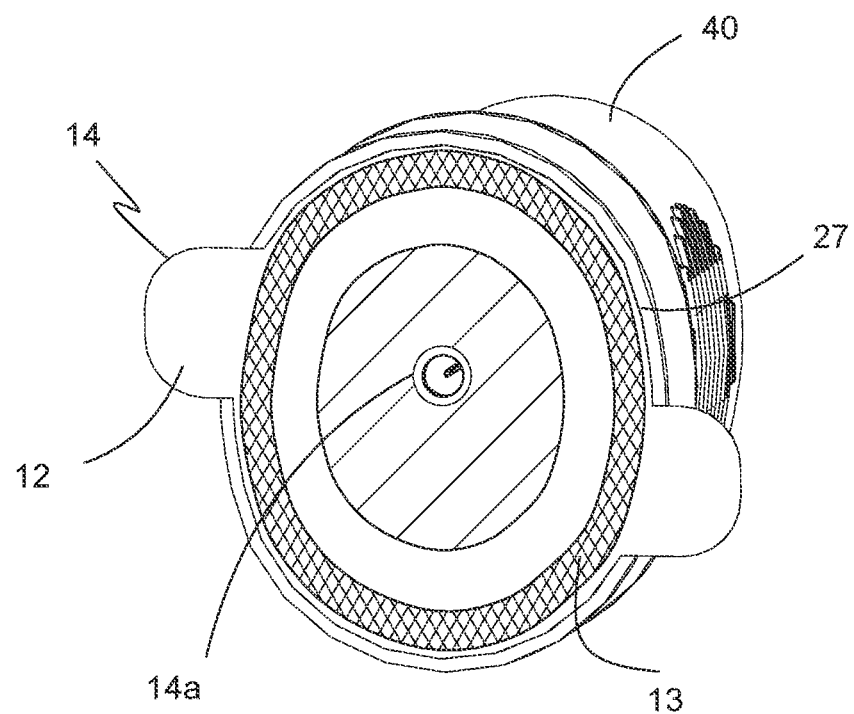
FIG. 1B is a bottom perspective view of the applicator of FIG. 1 showing the adhesive pad.
Figure 74:
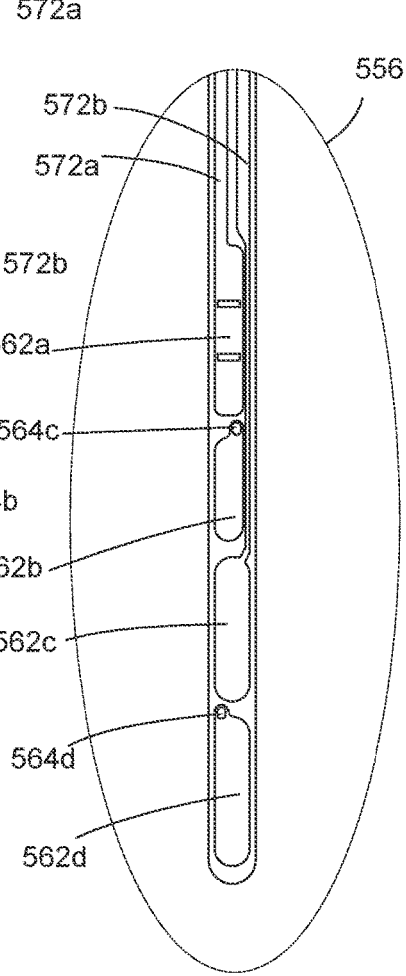
FIG. 74 is an enlarged view of the sensor end portion of FIG. 72.

The present invention is illustrated in FIGS. 1-74. FIG. 1 is a front perspective view of one embodiment of a ready-to-use subcutaneous sensor applicator 10. FIG. 1B is a bottom perspective view of applicator 10 showing a single-sided adhesive pad 14 with an adhesive pad cover 12. As shown, the adhesive pad cover 12 is clear only for the purpose of showing the location of an adhesive layer 13, but adhesive pad cover 12 may be opaque. As illustrated, an adhesive layer 13 of adhesive pad 14 aligns with an external housing flange portion 27 of applicator housing 21 and an adhesive pad opening 14a that aligns with a needle axis L2 (shown in FIGS. 32-33). The non-adhesive side of the single-sided adhesive pad 14 is bonded to lower housing bottom 172 (shown in FIG. 22) of a sensor lower housing 170 by welding. FIGS. 2 and 3 are front plan and left side plan views of the applicator 10, respectively, showing a vertical axis L1 that extends through the middle of sensor applicator 10. The ready-to-use subcutaneous sensor applicator 10 includes an applicator housing assembly 20 and a deployment button assembly 40. A unique feature of the present invention over other similar devices is that the ready-to-use subcutaneous sensor applicator 10 is fully assembled where a user does not need to combine any structural components before use. The user simply removes the ready-to-use subcutaneous sensor applicator 10 from its packaging, removes the adhesive tape cover 12 from the adhesive tape 14 on the bottom of the applicator housing 20 exposing the adhesive that is aligned with the proximal external body flange portion 27, positions the subcutaneous sensor applicator in a pre-selected location onto the user's skin or the skin of a patient, and pushes the deployment button assembly 40. The single push of the deployment button assembly 40 causes a sensor module 160 (not shown; see FIGS. 3 and 61-62) to be deployed onto the skin with an analyte sensor deployed subcutaneously in the skin and the power to the electronic circuit to be turned on automatically. The user is not required to assemble a sensor module to the applicator, or manipulate structure on the applicator to remove the deployment button assembly from the sensor module, or to perform any other task to power up the electronic circuit within the sensor module after subcutaneous insertion of the sensor.

Figure 4:
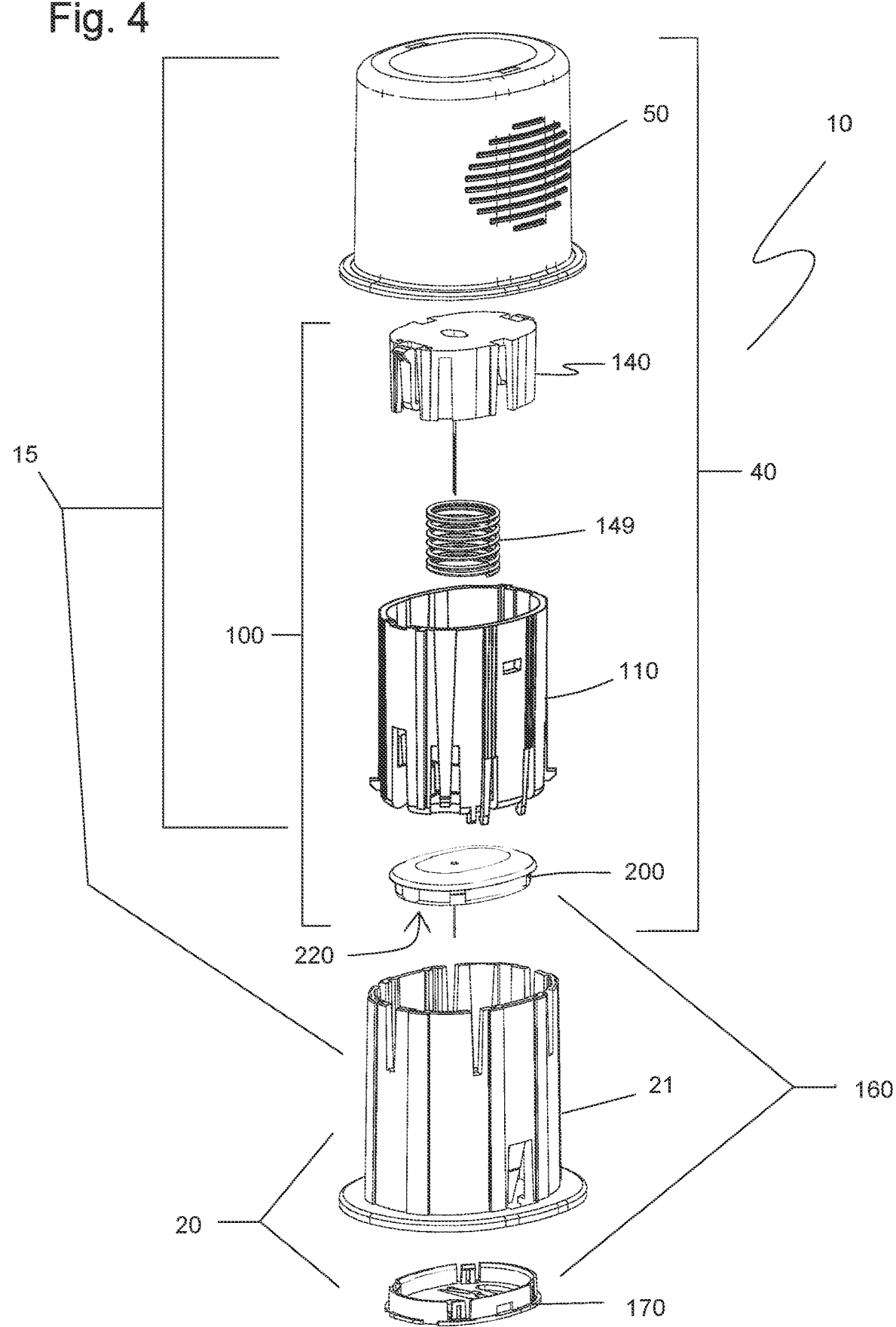
FIG. 4 is an exploded view of the applicator of FIG. 1.

Turning now to FIG. 4, there is illustrated an exploded, front, perspective view of the applicator 10. Applicator 10 includes an applicator module 15 and an unassembled sensor module 160. The applicator module 15 includes the button deployment assembly 40, which includes a pre-loaded insertion assembly 100, and the applicator housing assembly 20.

The pre-loaded insertion assembly 100 includes an insertion assembly housing 110, a needle assembly 140, a biasing element 149 and an electro-sensor assembly 220. The needle assembly 140 and the biasing element 149 are disposed within the insertion assembly housing 110 with the biasing element 149 compressed into a tensioned orientation such that the needle assembly 140 is in a ready or cocked position, and the insertion assembly housing 110 being locked within the deployment button 50. The electro-sensor assembly 220 is captured by the insertion assembly housing 110 at a lower or proximal end of the insertion assembly housing 110 such that a portion of sensor 250 is removably positioned within the needle 155 of the needle assembly 140 when the needle assembly 140 is in the ready or cocked position.

The applicator housing assembly 20 includes an applicator housing 21 and a sensor lower housing 170 captured by the applicator housing 21, which sensor lower housing 170 is released from the applicator housing 21 when the sensor applicator system is deployed. As shown in FIGS. 1-3, the deployment button assembly 40 is coupled to the applicator housing assembly 20 such that a portion of the insertion assembly housing 110 is within the applicator housing 21 and a portion of the applicator housing 21 is within the deployment button 50. The various assembled structural components will now be described individually.

Turning now to FIGS. 5-10, there is illustrated various views of deployment button 50. FIG. 5 is a front, left-side, perspective view of deployment button 50. Deployment button 50 has a button elongated body 52, a closed button distal end 53 and an optional button body flange 56 disposed at an open button proximal end 54. The button elongated body 52 has a circumferential wall 57 that defines a button chamber 58. FIG. 6 is a front plan view of the deployment button of FIG. 5. As can be seen from FIGS. 5-10, button elongated body 52 has a length BL that is longer than a width BW. The length BL is about 1.5 inches (3.8 cm) but this dimension is not limiting. The width BW is about 1.25 inches (3.2 cm) but this dimension is not limiting. The button chamber has a depth BD of about 1.4 inches (3.5 cm) but this dimension is not limiting. As shown in FIGS. 5-6 and 8, the sides of button elongated body 52 may include ridges or grooves 59 to provide better gripping of the deployment button 50 by the fingers and thumb of the user when placing on the skin of the user/patient.

FIG. 7 is a cross-sectional view of the deployment button of FIG. 5 taken along line F7-F7. Within button chamber 58, a plurality of optional elongated spacers 70 extend a predefined distance from closed button distal end 53 toward open button proximal end 54. Also within button chamber 58, there is an optional spacer wall 72 that extends a predefined distance from closed button distal end 53 toward open button proximal end 54 along the inside of circumferential wall 57. Spacer wall 72 is located within button chamber 58 such that a space is created between the plurality of elongated spacers 70 and spacer wall 72, which this space is only provided for ease of assembly during manufacturing.

FIG. 8 is a cross-sectional view of the deployment button of FIG. 5 taken along line F8-F8. In addition to the plurality of optional elongated spacers 70 and the optional spacer wall 72 are at least a pair of outward-facing button retaining arms 60. Button retaining arms 60 are connected to closed button distal end 53 and extend within button chamber 58 a predefined distance in the space created between the plurality of elongated spacers 70 and spacer wall 72. Button retaining arms 60 are resilient such that they can be bent toward a center of the button chamber 58 and return back to their original position. At the retaining arm's end is a button retaining arm hook structure 61. As shown in FIGS. 7 and 8, closed button distal end 53 has an optional recess 53a in an outside surface for placement of an index finger, if so desired, when activating the subcutaneous analyte sensor applicator system 10.

FIG. 9 is a top view of deployment button 50. In this view, a pair of optional closed end ports 53b is illustrated and looking down through the optional closed end ports 53b, one can see the hook structure 61 of the button retaining arms 60. The openings 53b are a result of the molds used when injection molding the part.

FIG. 10 is a bottom view of deployment button 50. In this view, the relationship of the plurality of elongated spacers 70 and spacer wall 72 is more clearly shown including the button retaining arms 60 and the optional button flange 56.

Turning now to FIGS. 11-16, the structure of the applicator housing 21 will now be discussed. FIG. 11 is a front, left-side, perspective view of applicator housing 21 and FIG. 12 is a front plan view of applicator housing 21. Application housing 21 has an applicator elongated body 22 formed by an applicator circumferential wall 25 that defines an applicator housing chamber 28, an open distal body end 23, an open proximal body end 24, a proximal internal body flange portion 26 (shown in FIG. 15), and a proximal external body flange portion 27. The proximal external body flange portion 27 is an important feature of the applicator 10. The purpose of the flange is that it passively applies solid even pressure on the adhesive tape using the deployment force of the mechanism. The resultant force of the 3-5 lbs. of deployment force is intentionally used to solidly set the pressure sensitive adhesive (PSA) of the adhesive tape on the skin of the user/patient. This is an important aspect of the present invention that achieves the entire integrated passiveness of the mechanism for the user. The user does not have to apply pressure to the adhesive tape to secure it to the skin of the user/patient after the sensor and applicator are simultaneously inserted and released, respectively. Applicator housing 21 also includes an inwardly-facing applicator housing retaining arms 30 formed in the applicator circumferential wall 25 where the applicator housing retaining arm 30 extend at a predefined angle from the applicator circumferential wall 25 into the applicator housing chamber 28 and terminate adjacent the open proximal body end 24. Applicator housing retaining arm 30 is sufficiently resilient so that the arm 30 can be forced back toward the circumferential wall 25. A plurality of spacer slots 39 extend from open distal body end 23 of the applicator elongate body 22 a predefined distance sufficient to accommodate the plurality of elongated spacers 70 of the deployment button 50.

FIG. 13 is a cross-sectional view of the applicator housing of FIG. 11 taken along line F13-F13. Besides the inward-facing applicator housing retaining arm 30, there are two other features along the inside surface of the applicator circumferential wall 25. These features include an elongated cam wall surface 32 and an applicator assembly housing stop 38. FIG. 13A is an enlarged view of the cam wall surface 32 delineated by area F13A. As can be seen, an upper surface portion 32a has as a first surface portion recess 33, a first sloping surface 34a that extends along the cam wall surface 32 away from surface portion recess 33 and slopes toward the applicator housing chamber 28, a second sloping surface 34b that extends along cam wall surface 32 away from first sloping surface 34a and slopes away from the applicator housing chamber 28. A cam surface 36 extends along middle surface portion 32b and away from second sloping surface 34a and slopes further away from the applicator housing chamber 28 where cam surface 36 terminates at a lower surface portion 32c that has a second surface portion recess 35. FIG. 13B is an enlarged view of the insertion assembly housing stop 38 delineated by area F13B. Insertion assembly housing stop 38 is located to create an endpoint for the movement of deployment housing assembly 40 when deployment button 50 is activated. FIG. 14 is a cross-sectional view of applicator housing of FIG. 11 taken along line F14-F14. This view illustrates the inward-facing applicator housing retaining arms 30 with their retaining arm hook ends 30a and shows the retaining arms 30 as they extend at a predefined angle toward open proximal body end 24.

FIG. 15 is a top view of applicator housing 21. This view shows the retaining arm hook ends 30a as well as the proximal internal body flange portion 26. In FIG. 16, proximal internal body flange portion 26 has a flange portion recess 26a. This recess is designed to accommodate the sensor lower housing 200 for the purpose of presenting coplanar surfaces between open proximal body end 24 and sensor lower housing 200 while inward-facing applicator housing retaining arms 30 hold sensor lower housing 200 until the subcutaneous analyte sensor applicator system is deployed.

Turning now to FIGS. 17-22, there is illustrated various views of one embodiment of sensor lower housing 170. FIGS. 17 and 18 are a front, left, perspective view and a front plan view of sensor lower housing 170, respectively. Sensor lower housing 170 has a lower housing bottom 172, a lower housing wall 173 that extends upward from lower housing bottom 172 defining a lower housing chamber 184, and a circumferential bottom flange 171 that extends perpendicularly away from lower housing wall 173. In at least two, opposed locations in lower housing wall 173, there is a lower housing locking element 174 that is inwardly facing and used to retain sensor upper housing 200 and electro-sensor assembly 220 after deployment of the applicator system 10. Also in at least two, opposed locations in lower housing wall 173, there is a lower housing retainer recess 178 for receiving applicator housing retaining arm 30 for holding sensor lower housing 170 at open proximal body end 24 of applicator housing 21 prior to deployment of the applicator system 10. Also shown are a plurality of optional flange notches 182 in circumferential bottom flange 171, which are not required, and used only for ease of assembly of sensor lower housing 170 to applicator housing 21 and is not an essential aspect of the present invention. Extending into lower housing chamber 184 from lower housing bottom 172 is a power actuator 175 that contacts a power switch on the electro-sensor assembly 220 when sensor upper and lower housings 170, 200 are joined together when the sensor applicator system 10 is deployed. In this embodiment, power actuator 175 is resilient such that it has a bowed cross-sectional shape from lower housing bottom 172 into lower housing chamber 184. This is shown in FIG. 20A. The bowed shape provides a biasing tension by the power actuator 175 to the power switch 240 (shown in FIG. 44) on electronic circuit 230 when the sensor applicator system is deployed such that the joining of sensor upper and lower housings 170, 200 causes the power switch 240 to depress power activator 175, which, in turn, maintains a biasing force against power switch 240.

FIGS. 19 and 20 are a cross-sectional view of sensor lower housing 170 of FIG. 17 taken along line F19-F19 and a cross-sectional view of sensor lower housing 170 of FIG. 17 taken along line F20-F20. These views provide a more clear view of the inwardly-facing lower housing locking elements 174, the lower housing retaining recess 178 and the power actuator 175.

FIGS. 21 and 22 are a top plan view and a bottom plan view of lower sensor housing 170, respectively. In this embodiment, there are three openings 176 references as vent openings 176a, 176b and sensor opening 176c. Sensor opening 176c is for accommodating the subcutaneous sensor 250 when the sensor applicator system is deployed. Openings 176a and 176b are optional and may provide ventilation to the patient's skin to allow trapped moisture to wick out of the sensor housing 170.

Figure 23:
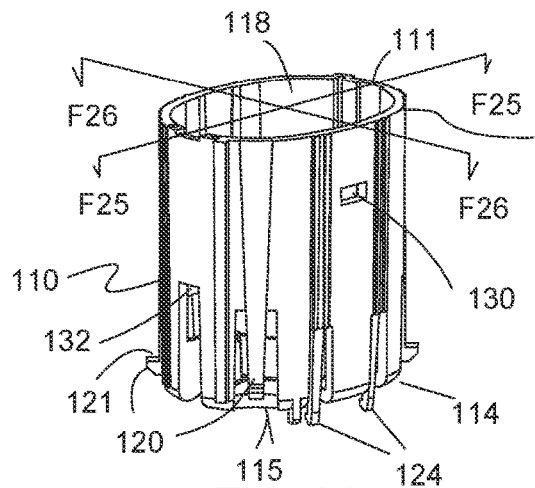
FIG. 23 is a front perspective view of one embodiment of an insertion assembly housing of the applicator of FIG. 4.
Figure 24:
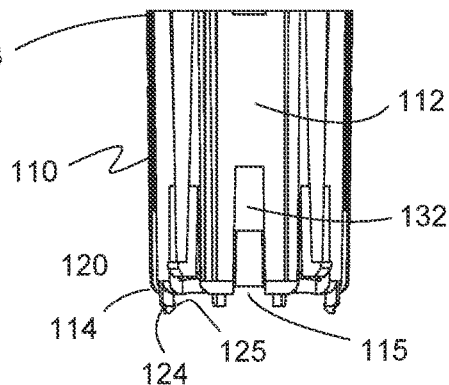
FIG. 24 is a front plan view of the insertion assembly housing of FIG. 23.

Turning now to FIGS. 23-29, there are illustrated various views of one embodiment of the insertion assembly housing 110. FIGS. 23 and 24 are a front perspective view and a front plan view of the insertion assembly housing 110. Insertion assembly housing 110 includes an assembly housing body 112, an open housing distal end 113, a closed housing proximal end 114, an assembly housing bottom 115, and an assembly circumferential wall 111 defining an assembly housing chamber 118. Assembly circumferential wall 111 includes an assembly housing locking slot 130 spaced from open housing distal end 113 that receives outwardly facing button retaining arm 60 when insertion assembly housing 110 is assembled into deployment button 50. Once insertion assembly housing 110 is inserted and retained within deployment button 50, it remains locked within deployment button 50 and always moves with the deployment button 50.

Assembly circumferential wall 111 also includes a plurality of assembly housing retaining arms 120 where each of the retaining arms 120 have an outward-facing housing arm hook surface 121. The retaining arms 120 reside in first surface portion recess 33 of the elongated cam wall surface 32 and lock insertion assembly housing 110 within applicator housing 21, which effectively locks deployment button 50 to applicator housing 21 by way of the button retaining arms 60 of deployment button 50 being locked into assembly housing locking slot 130 of the assembly circumferential wall 111 of insertion assembly housing 110. During deployment of the sensor applicator system, each assembly housing retaining arm 120 slides along the elongated cam wall surface from the first surface portion recess 33 when in the ready-to-use orientation to the second surface portion recess 35 when in the deployed orientation.

Another aspect of assembly circumferential wall 111 includes a plurality of housing retaining fingers 124 where each retaining finger 124 has an inward-facing finger hook surface 125. Each retaining finger 124 extends below assembly housing bottom 115 and holds sensor upper housing 200 when the sensor applicator system 10 is in the ready-to-use orientation. Circumferential wall 111 also includes a needle assembly locking slot 132 that extends a predefined distance from closed housing proximal end 114 toward open housing distal end 113. Needle assembly locking slot 132 is to accommodate the applicator assembly housing stop 38 of applicator housing 21, which will interact with needle assembly 140 (to be discussed later) when sensor applicator system 10 is deployed to insert subcutaneous sensor 250.

Figure 25:
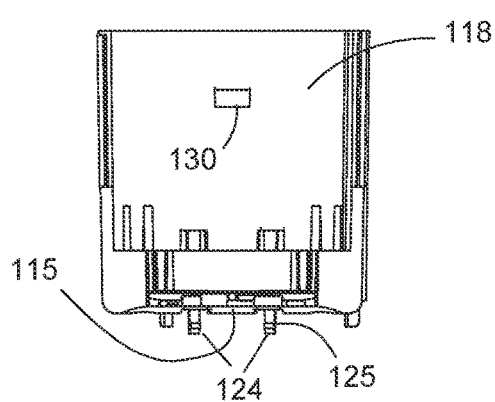
FIG. 25 is a cross-sectional view of the insertion assembly housing of FIG. 23 taken along line F25-F25.
Figure 26:
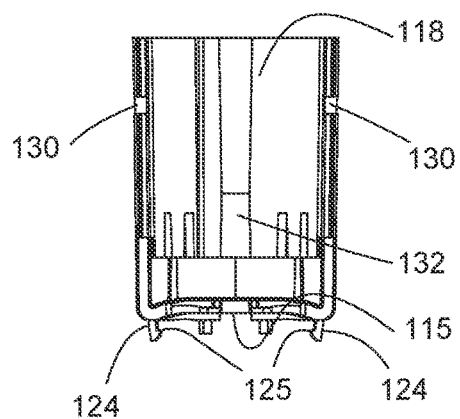
FIG. 26 is a cross-sectional view of the insertion assembly housing of FIG. 23 taken along line F26-F26.

Turning now to FIGS. 25 and 26, there is illustrated a cross-sectional view of insertional assembly housing 110 taken along ling F25-F25 and F26-F26, respectively. As shown in these figures, assembly housing bottom 115 is recessed to accommodate sensor upper housing 200 while the plurality of housing retaining fingers 124 hold sensor upper housing 200 within the recessed housing bottom 115 until released by activation of the sensor applicator system 10.

Figure 27:
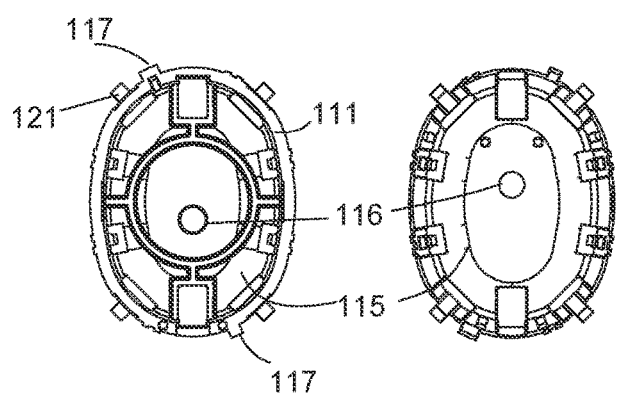
FIG. 27 is a top view of the insertion assembly housing of FIG. 23.
Figure 28:
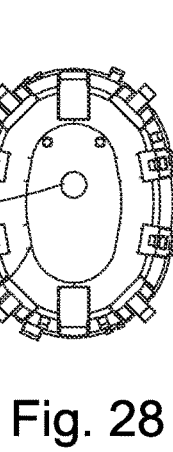
FIG. 28 is a bottom view of the insertion assembly housing of FIG. 23.
Figure 29:
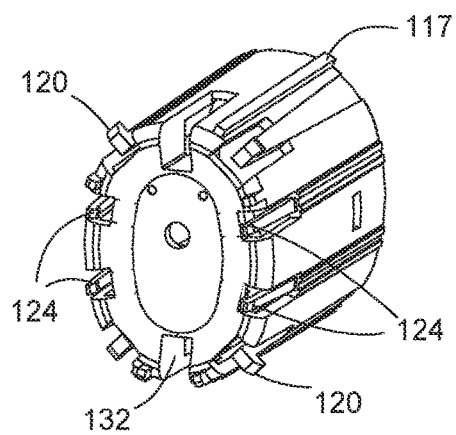
FIG. 29 is a bottom perspective view of the insertion assembly housing of FIG. 23.

FIGS. 27 and 28 illustrate a top view and a bottom view of insertion assembly housing 110. In these views, it is clearly shown that outward-facing housing arm hook surface 121 of assembly housing retaining arm 120 extend beyond the perimeter of assembly circumferential wall 111 for engagement with elongated cam wall surface 32 of applicator housing 21 and the existence of a housing proximal end opening 116 to accommodate the needle 155 of the needle assembly 140. Also shown is at least one optional assembly housing rail 117 that also extends along a major portion of assembly circumferential wall 111 between open housing distal end 113 and closed housing proximal end 114, and beyond the perimeter of assembly circumferential wall 111. This optional rail 117, if included, would be disposed within a corresponding applicator housing channel 29 to facilitate alignment of insertion assembly housing 110 within applicator housing 21. FIG. 29 is a bottom perspective view of the insertion assembly housing 110 to provide a visual of the structural relationship of the assembly housing bottom 115, the assembly housing retaining arm 120, the housing retaining finger 124, and needle assembly locking slot 132.

Figure 30:
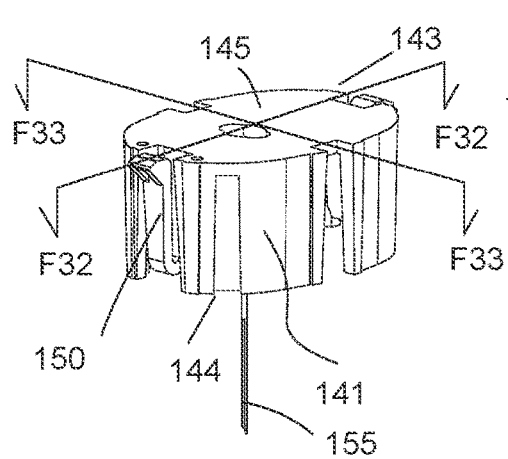
FIG. 30 is a front perspective view of one embodiment of a needle assembly of the applicator.
Figure 31:
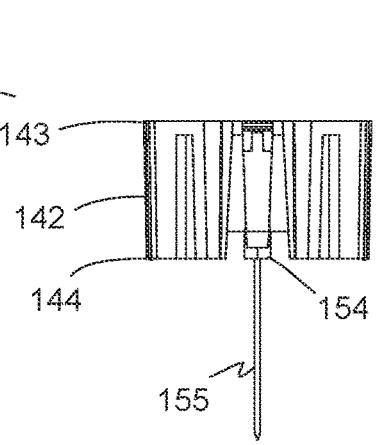
FIG. 31 is a front plan view of the needle assembly of FIG. 30.

Turning now to FIGS. 30-35, there is illustrated various views of one embodiment of a needle assembly 140. FIGS. 30 and 31 are a front perspective view and a front plan view of needle assembly 140. Needle assembly 140 includes a needle body 142 and a tubular needle 155 with a needle wall 155*a* (not shown) fixedly attached to needle body 142 where the tubular needle 155 defines a needle axis L2 (shown in FIGS. 32, 32).

Figure 32:
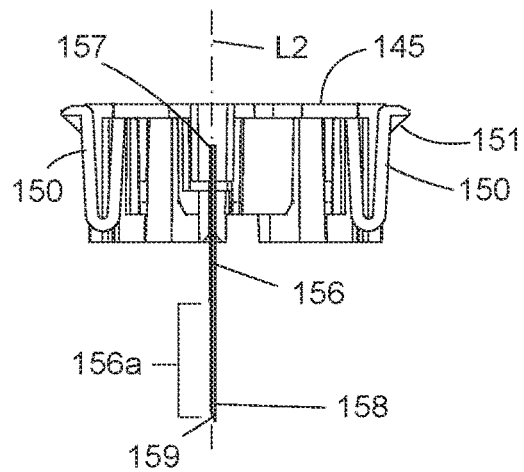
FIG. 32 is a cross-sectional view of the needle assembly of FIG. 30 taken along line F32-F32.
Figure 33:
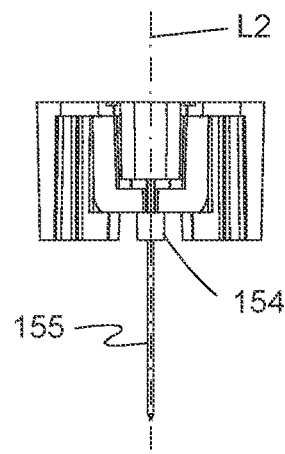
FIG. 33 is a cross-sectional view of the needle assembly of FIG. 30 taken along line F33-F33.

FIGS. 32 and 33 illustrate a cross-sectional view of the needle assembly of FIG. 30 taken along line 32-32 and a cross-sectional view of the needle assembly of FIG. 30 taken along line 33-33, respectively. Needle 155 is located to align with housing proximal end opening 116 of insertion assembly housing 110. Needle body 142 has a closed needle body distal end 143, an open needle body proximal end 144, a needle body top 145, a needle body retaining arm 150, and a needle-receiving portion 154. Needle 155 has a needle wall 155*a* that forms a needle body 156 with a needle distal end 157 and a needle proximal end 158. Needle distal end 157 is fixedly secured to needle-receiving portion 154 of needle body 142. More specifically, the needle is fixated to the needle-receiving portion 154 with tight tolerance. A usable securing material is UV epoxy. This fixation is important because the portion of the needle wall that's removed must align closely with sensor 250. Needle proximal end 158 includes a needle sharp 159. Needle 155 includes a needle open region 156*a* where a portion of the needle wall 155*a* is removed. Needle open region 156*a* extends from needle proximal end 158 for a predefined distance. Needle open region 156*a* is needed to accommodate sensor 150 and to allow retraction of needle 155 after deployment of sensor 150 subcutaneously. FIG. 32 shows the structure of needle body retaining arm 150 where retaining arm 150 has an outward-facing needle retaining arm hook surface 151 that extends beyond the needle body circumferential wall 141 when needle body retaining arm 150 is in a relaxed state. Needle body retaining arm 150 is resilient and configured such that it may be compressed toward and into needle body circumferential wall 141. FIG. 33 shows one embodiment of needle receiving portion 154 of needle body 142. Needle receiving portion 154 is configured to delineate an area around which biasing element 149 resides between closed needle body distal end 143 and closed housing proximal end 114 of the insertion assembly housing 110. When needle assembly 140 is assembled inside of assembly housing chamber 118 of the insertion assembly housing 110, biasing element 149 is in a compressed state and needle body retaining arm 150 is located within and held by needle assembly locking slot 132 of insertion assembly housing 110 until released by interference with applicator assembly housing stop 38 of applicator housing 21 when deployment button assembly 40 is deployed to insert sensor 250 subcutaneously. When applicator assembly housing stop 38 forces needle body retaining arm 150 into needle body 142, biasing element 149 moves to a less compressed state causing needle assembly 140 to slide toward open housing distal end 113 causing needle 155 to retract away from upper sensor housing 200.

Figure 34:
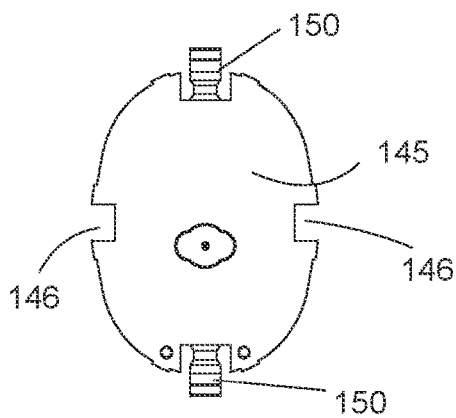
FIG. 34 is a top view of the needle assembly of FIG. 30.
Figure 35:
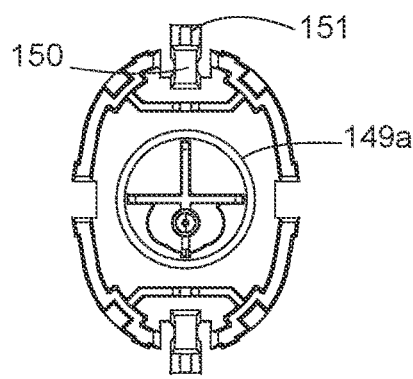
FIG. 35 is a bottom view of the needle assembly of FIG. 30.

FIGS. 34 and 35 are a top view and a bottom view of needle assembly 140. These views show the position of the needle body retaining arm 150 relative to the needle body 142. Also shown are needle body side slots 146 that are included for two reasons: (a) to prevent any inadvertent disconnection of outwardly-facing button retaining arm 60 of the deployment button 50 from the assembly housing locking slot 130 and (b) to prevent possible interference with needle body 142 as it slides up toward deployment button top 55 after implanting sensor 250 into subcutaneous tissue. In the bottom view, an outline 149*a* of the biasing element 149 is provided to show the relative position of the biasing element 149 against the inside top surface of the needle body top 145.

Figure 36:
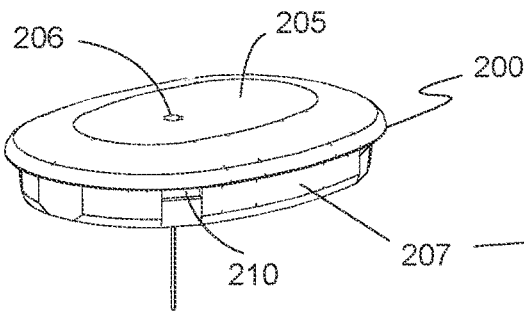
FIG. 36 is a front, top, perspective view of one embodiment of a sensor upper housing containing one embodiment of an electro-sensor assembly.
Figure 37:
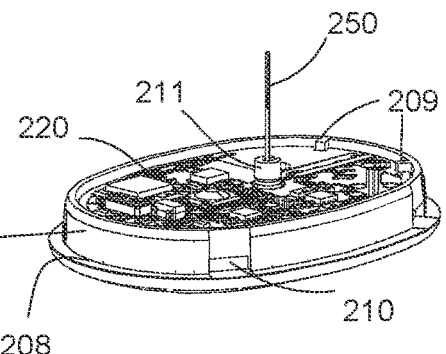
FIG. 37 is a rear, bottom, perspective view of the sensor upper housing and the electro-sensor assembly of FIG. 36.
Figure 36A:
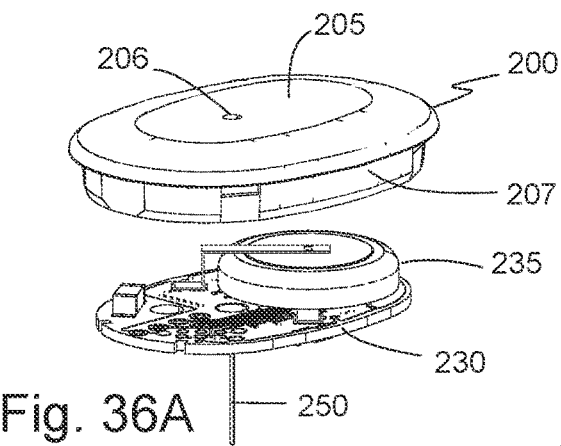
FIG. 36A is an exploded view of the inserter assembly of FIG. 36.

Turning now to FIGS. 36 and 37, there is illustrated a front, top, perspective view and a rear, bottom, perspective view of one embodiment of a sensor upper housing 200 containing an electro-sensor assembly 220. The electro-sensor assembly 220 includes an electronic circuit 230 and a sensor 250. FIG. 36 shows a subcutaneous sensor 250 extending a predefined distance below sensor upper housing 200. FIG. 37 shows electro-sensor assembly 220 residing within sensor upper housing 200. After the electro-sensor assembly 220 is assembled within sensor upper housing 200, a potting compound 215 is applied by an automatic dispensing machine (not shown) to the sensor upper housing 200. The potting compound 215 seeps down under the electronic circuit 230 and is filled until the potting compound 215 is just even with the base of the activation switch 240 (shown in FIG. 44) and flows out to the inner circumference to the sensor upper housing 200 and the electronic circuit retainer 209. The potting compound is typically a waterproof material, preferably a 2-part fast-curing material. FIG. 36A is an exploded view of FIG. 36 showing electro-sensor assembly 220 and sensor upper housing 200.

Figure 38:
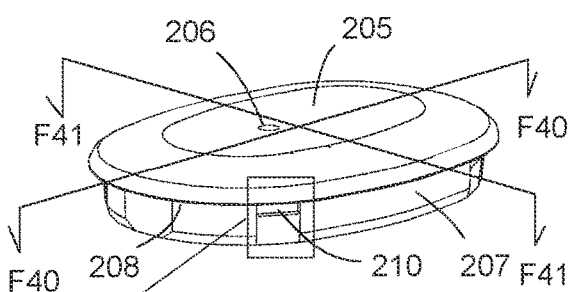
FIG. 38 is a front, top, perspective view of the sensor upper housing of FIG. 36.
Figure 38A:
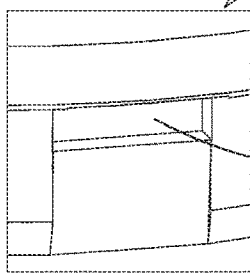
FIG. 38A is an enlarged view of an upper housing retaining recess.
Figure 39:
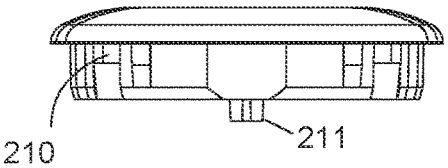
FIG. 39 is a front plan view of the sensor upper housing of FIG. 38.

FIGS. 38, 38A and 39 are a front, perspective view, an enlarged view of an upper housing retaining recess and a front plan view, respectively, of sensor upper housing 200. Sensor upper housing 200 has an upper housing top 205, an upper housing top opening 206, a circumferential upper housing wall 207 that extends transversely away from upper housing top 205 and defines an upper housing chamber 212 (shown in FIGS. 40, 41), and a housing top flange portion 208 that extends from upper housing top 205 transversely beyond circumferential upper housing wall 207. Circumferential upper housing wall 207 also includes an upper housing locking recess 210 adjacent housing top flange portion 208. Upper housing locking recess 210 is located for locking engagement with a corresponding lower housing locking element 174 when joined together to form sensor module 160 is deployed on a user's skin. On the inside of circumferential upper housing wall 207 is at least one electronic circuit retainer 209 that holds the electronic circuit 230 within upper housing chamber 212.

Figure 40:
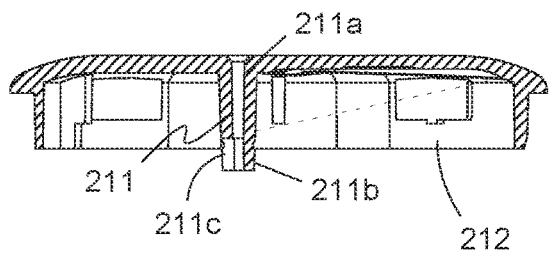
FIG. 40 is a cross-sectional view of the sensor upper housing of FIG. 38 taken along line F40-F40.
Figure 41:
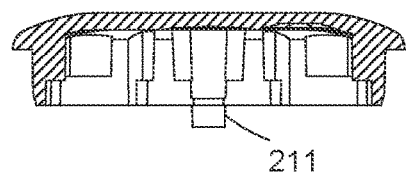
FIG. 41 is a cross-sectional view of the sensor upper housing of FIG. 38 taken along line F41-F41.

FIGS. 40 and 41 are a cross-sectional view of the sensor upper housing of FIG. 38 taken along line F40-F40 and a cross-sectional view of the sensor upper housing of FIG. 38 taken along line F41-F41, respectively. Descending from upper housing top opening 206 is a tubular upper housing needle guide 211. Upper housing needle guide 211 has a guide distal end 211a and a guide proximal end 211b. Furthermore, the needle guide 211 extends a predefined distance such that, when sensor upper housing 200 is coupled with sensor lower housing 170, guide proximal end 211b of upper housing needle guide 211 extends no further than lower housing bottom 172. Guide proximal end 211b has a portion 211c removed to accommodate sensor 250, which has a bend that is positioned within portion 211c and where a portion of sensor 250 is positioned within the needle open region of needle 155. FIG. 41 is a cross-sectional view of the sensor upper housing of FIG. 38 taken along line F41-F41 showing the upper housing locking recess 210.

Turning now to FIGS. 42 and 43, there is illustrated the electronic circuit 230 without sensor 250. FIG. 42 is a bottom perspective view and FIG. 43 is a top perspective view. FIG. 43 clearly shows the battery 235 that powers electronic circuit 230. FIG. 42 shows a circuit power switch 240 that is in a normally off position. FIG. 44 is an enlarge view area F44 delineated in FIG. 42. Circuit power switch 240 is a frusto-conical shape above adjacent electronic components of the electronic circuit 230. Circuit power switch 240 is positioned on electronic circuit 230 to couple with the power actuator 175 of sensor lower housing 170 when sensor upper housing 200 and sensor lower housing 170 are coupled together during sensor applicator system activation and deployment. When coupled together, power actuator 175 pushes against circuit power switch 240 which then connects power from battery 232 to electronic circuit 230 and sensor 250. The sensor module 160 is automatically powered on when this action occurs. In other words, this action automatically occurs when the sensor applicator system 10 is deployed and the sensor module 160 deployed on the skin of the user with the sensor implanted subcutaneously. Electronic circuit 230 also includes electronic components such as, for example, a transmitter (not shown) for wireless communication of sensor and other data with an electronic device 902 such as those devices described later.

FIGS. 45 and 46 are front and rear views of one embodiment of sensor 250, respectively. Sensor 250 has a sensor distal end 260, a sensor middle portion 270 and a sensor proximal portion 280. Sensor distal end 260 has a plurality of contact pads 262 that electrically couples to electronic circuit 230. Sensor proximal portion 280 along with a portion of sensor middle portion 270 is implanted subcutaneously within the skin of the user/patient. A plurality of electrodes 282 are exposed at sensor proximal portion 280 where at least one of the plurality of electrodes 282 is configured to measure an analyte, such as, for example, glucose. More than one analyte may be measured provided that other of the plurality of electrodes 282 are so configured. In this embodiment, sensor 250 has a bend such that sensor proximal portion 280 is transverse, and preferably perpendicular, to sensor distal end 260.

FIG. 47 is an enlarged, rear view of sensor 250 showing sensor proximal portion 280 and the plurality of electrodes 282 with sensor distal portion 260 extending away from the viewer and into the plane of the drawing. As seen, this embodiment of sensor 250 has one or more friction surfaces 284 that appear as bumps along the side of sensor proximal portion 280. These "bumps" contact the inside surface of needle wall 155a in needle open region 156a. The frictional contact between sensor proximal portion 280, needle wall 155a and the size of sensor 250 allow needle 155 to penetrate the skin of the user and implant sensor proximal portion 280 subcutaneously without damaging sensor proximal portion 280 or any portion of sensor 250 and then withdraw needle 155 leaving sensor proximal portion 280 implanted.

Turning now to FIGS. 48-62, there will be discussed the operation of the all-inclusive, ready-to-use sensor applicator system 10. FIGS. 48 and 49 are cross-sectional views of the applicator system 10 in a ready-to-use state. FIG. 48 is a left-side, cross-sectional view of the applicator system 10 of FIG. 1 taken along line F48-F48 in FIG. 1 showing the applicator system is a ready-to-use state. As illustrated, sensor applicator system 10 is packaged as ready-to-use and is all-inclusive, meaning that the user does not need to assemble a "sensor module" to an inserter or to physically connect a power source to the sensor module to operate the sensor module (i.e. to power the electronic circuit and sensor). In this all-inclusive, ready-to-use position, the needle assembly 140 is coupled inside of the insertion assembly housing 110 with the biasing element 149 in a compressed state storing potential energy used for retracting the needle 155 once deployed. The sensor upper housing 200 is retained at the closed housing proximal end 114 of the insertion assembly housing 110. Needle 155 extends through upper housing needle guide 211 toward sensor lower housing 170 where needle proximal end 158 is position directly aligned with and adjacent the sensor opening 176c of sensor lower housing 170. FIG. 49 is a front, cross-sectional view of the applicator system of FIG. 1 taken along line F49-F49 in FIG. 1. This view shows outwardly-facing button retaining arms of deployment button 50 engaged in assembly housing locking slot 130 of insertion assembly housing 110. This is more clearly shown in FIG. 50A, which is an enlarged view within the area delineated by F50A in FIG. 549. This view also shows inwardly-facing applicator housing retaining arm 30 coupled to lower housing locking recess 178 to retain sensor lower housing 170 to application housing 21. This is more clearly shown in FIG. 50B, which is an enlarged view within the area delineated by F50B in FIG. 49.

Figure 51:
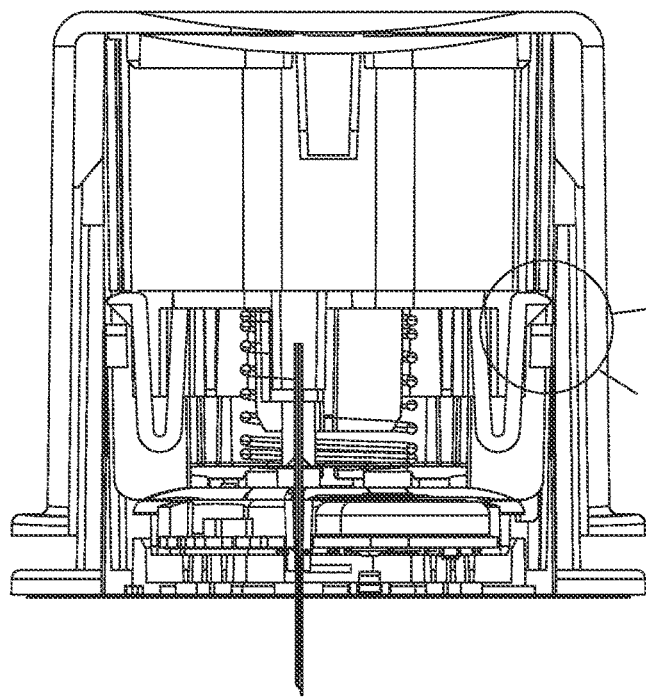
FIG. 51 is a left-side, cross-sectional view of the applicator system of FIG. 48 showing the applicator system partially deployed just before releasing contact of the various retaining arms.
Figure 52:
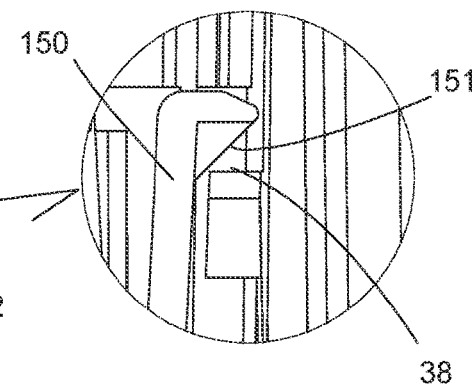
FIG. 52 is an enlarged, cross-sectional view of the applicator system of FIG. 51 within an area delineated as F52 showing an outward-facing needle retaining arm hook surface immediately before full deployment and needle body release.
Figure 53:
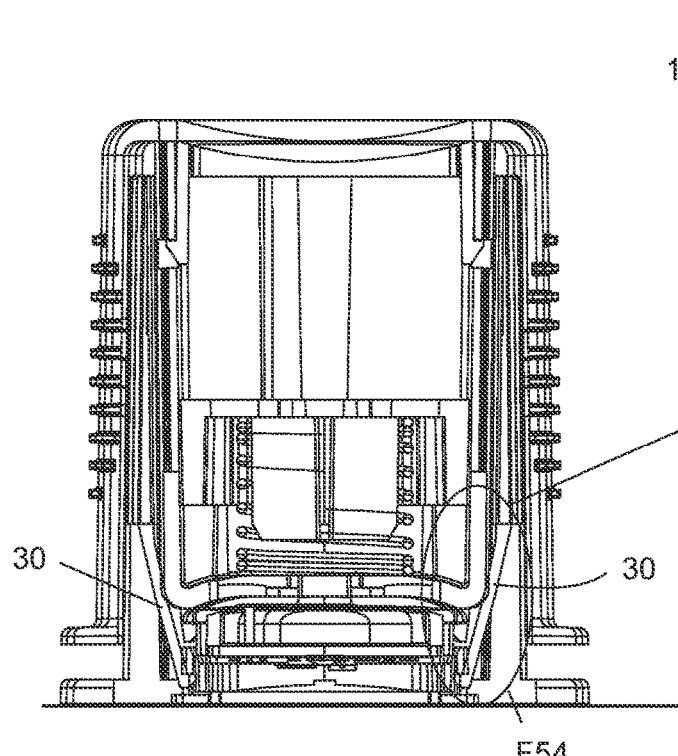
FIG. 53 is a front, cross-sectional view of the application system of FIG. 51.
Figure 54:
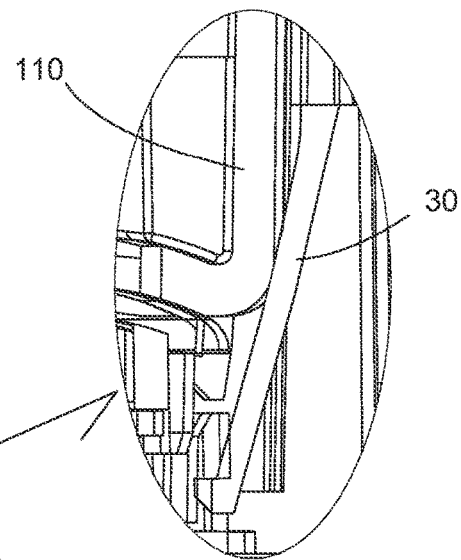
FIG. 54 is an enlarged, cross-sectional view of the applicator system of FIG. 53 within an area delineated as F54 showing an inward-facing applicator housing retaining arm immediately before full deployment and sensor module release.

FIGS. 51 and 53 are cross-sectional views of the applicator system 10 in a deployed orientation just before completion of the implantation of sensor 250 before needle 155 is retracted and the sensor upper and lower housings 170, 200 are joined to each other. The purpose is to show the spatial relationship of the relevant retaining arms and corresponding locking recesses of the various components where substantially simultaneously, the sensor module 160 is about to be completed, the needle 155 and sensor 250 are within the subcutaneous tissue of the user, the needle assembly 140 is about to be automatically retracted, and the sensor module 160 is about to be released from the applicator housing 21. FIG. 51 a left-side, cross-sectional view of the applicator system of FIG. 48 showing the applicator system partially deployed just short of full deployment. FIG. 52 is an enlarged view within the area delineated by F52 in FIG. 51 showing that the needle body retaining arm 150 is about to make contact with applicator assembly housing stop 38. FIG. 53 is a front, cross-sectional view of the application system of FIG. 51 showing the closed housing proximal end 114 of the insertion assembly housing 110 about to make contact with the inwardly-facing applicator housing retaining arm 30. FIG. 54 is an enlarged view within the area delineated by F54 in FIG. 53.

FIGS. 55 and 57 are cross-sectional views of the applicator system 10 in a deployed orientation upon completion of the implantation of sensor 250. FIG. 55 is a left-side, cross-sectional view of the applicator system of FIG. 48 showing the applicator system 10 fully deployed with the needle assembly 140 retracted within the insertion assembly housing 110. As shown, sensor upper housing 170 is coupled with sensor lower housing 200 and needle assembly 140 has been moved by the kinetic energy of released biasing element 149 where the needle body top 145 is in contact with deployment button top 55. FIG. 56 is an enlarged view within the area delineated by F56 in FIG. 55. FIG. 55 more clearly shows the contact between needle body top 145 and deployment button top 55. FIG. 57 is a front, cross-sectional view of the applicator system 10 of FIG. 55 fully deployed. In this view, closed housing proximal end 114 had made contact with inwardly-facing applicator housing retaining arm 30 and, at its furthest most travel, has completely pushed retaining arm 30 away from sensor lower housing 170, which releases the now formed sensor module 160 from the applicator module 15. FIG. 58 is an enlarged view within the area delineated by F58 in FIG. 57 to more clearly show how the retaining arm 30 is released from sensor lower housing 170.

Figure 59:
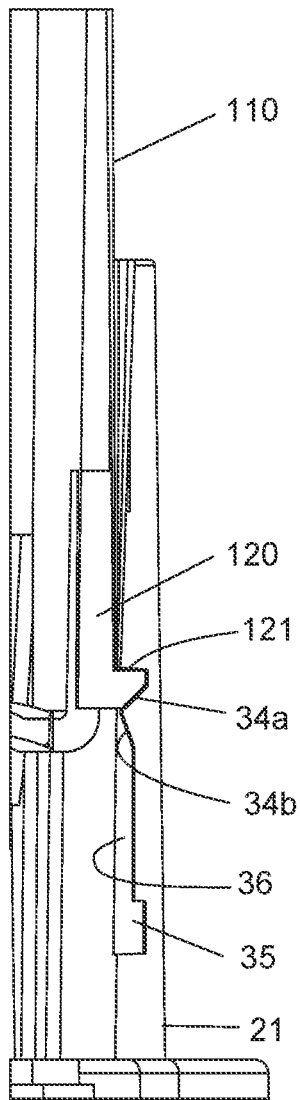
FIG. 59 is an enlarged cross-sectional view of the ready-to-use orientation of the assembly housing retaining arm and the elongated cam wall surface of the applicator housing.
Figure 60:
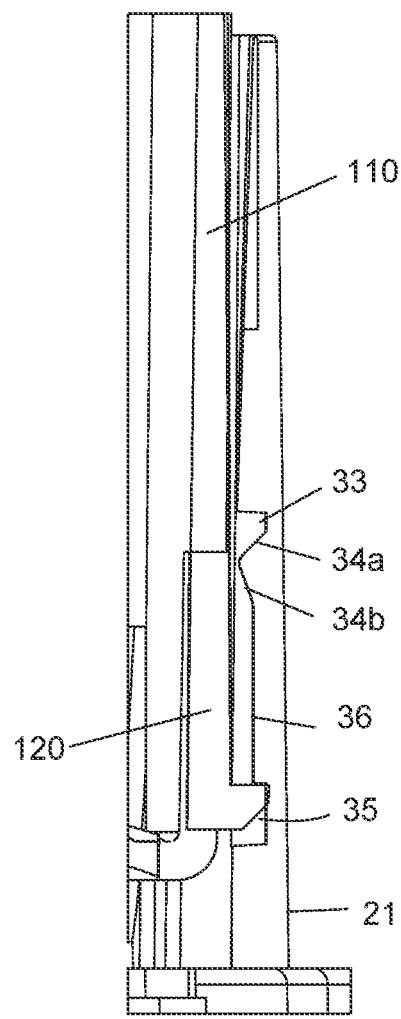
FIG. 60 is an enlarged cross-sectional view of the fully deployed orientation of the assembly housing retaining arm and the elongated cam wall surface of the applicator housing.

Turning now to FIGS. 59 and 60 are cross-sectional views of the ready-to-use orientation and the fully deployed orientation of the assembly housing retaining arm 120 and the elongated cam wall surface 32 of the applicator housing 21. At the ready-to-use orientation, a sufficient force against the deployment button 50 is required to overcome the resistance created by the first sloping surface 34a of the cam wall surface 32, which sloping surface 34a causes the assembly housing retaining arm 120 to push and bias the arm 120 toward the assembly housing chamber 118 (i.e. by riding/sliding along sloping surface 34a) until the assembly housing retaining arm 120 reaches second sloping surface 34b of the cam wall surface 32. The initial force applied against the deployment button 50 coupled with the force of the biased arm 120 causes the deployment button to continue to move without additional force required to its fully deployed position as the assembly housing retaining arm 120 follows along the second sloping surface 34b and the cam surface 36 which continues to slope away (i.e. outwardly) applicator housing chamber 28 until assembly housing retaining arm 120 reaches second surface portion recess 35 of the elongated cam wall surface 32. At this point downward movement of deployment button assembly 40 ceases since the sensor module 160 is fully deployed.

FIGS. 61 and 62 are a right-side plan view and a front plan view of the fully deployed sensor applicator system 10 showing the sensor module 160 deployed and separated from the applicator module 15 with sensor 250 deployed subcutaneously within the skin of the user/patient.

Needle/sharp

Figure 63:
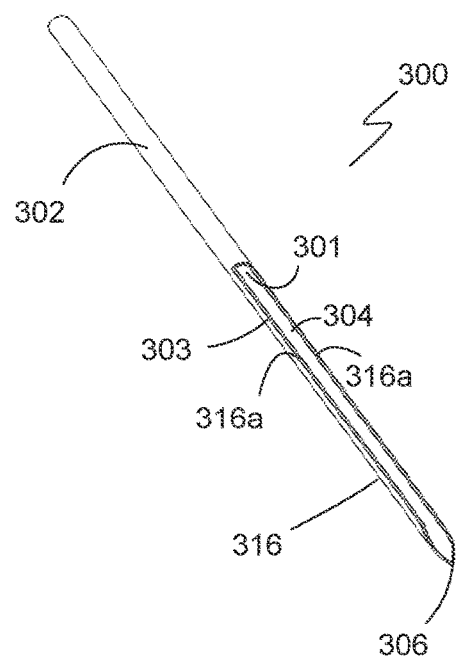
FIG. 63 is a perspective view of one embodiment of a sharp of the present invention showing the sharp tip, a sharp open region, and a portion of the sharp body.
Figure 64:
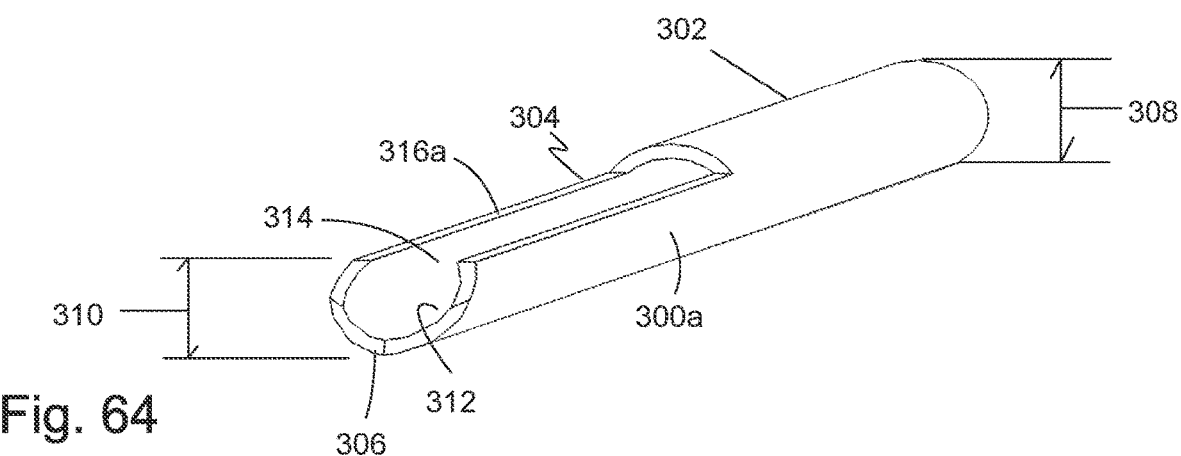
FIG. 64 is an end perspective view of the sharp of FIG. 64 showing the concave well defined by the sharp open region.

FIGS. 63 and 64 illustrate perspective views of one embodiment of a needle/sharp 300 of the present invention. Needle/sharp 300 includes a sharp body 302, a sharp open region 304, and a sharp tip 306. Sharp body 302 is an annular section of sharp 300 that extends longitudinally and defines an enclosed conduit 301 therethrough.

A wire EDM machining operation or a laser operation is used to remove a portion of the tubing wall 303 along sharp 300 a predefined distance to define sharp open region 304, thereby reducing the overall height 310 of sharp 300. Both the wire EDM machining operation and the laser operation can be performed on cylindrical tubing or on flattened, oval tubing. Sharp open region 304 is a section of an annulus that extends longitudinally with the tubing wall 303 along the length of sharp open region 304 defining an unenclosed concave well 314 from sharp tip 306 to sharp body 302. Concave well 214 is sized to receive a continuous monitoring sensor 250.

CGM System

Figure 65:
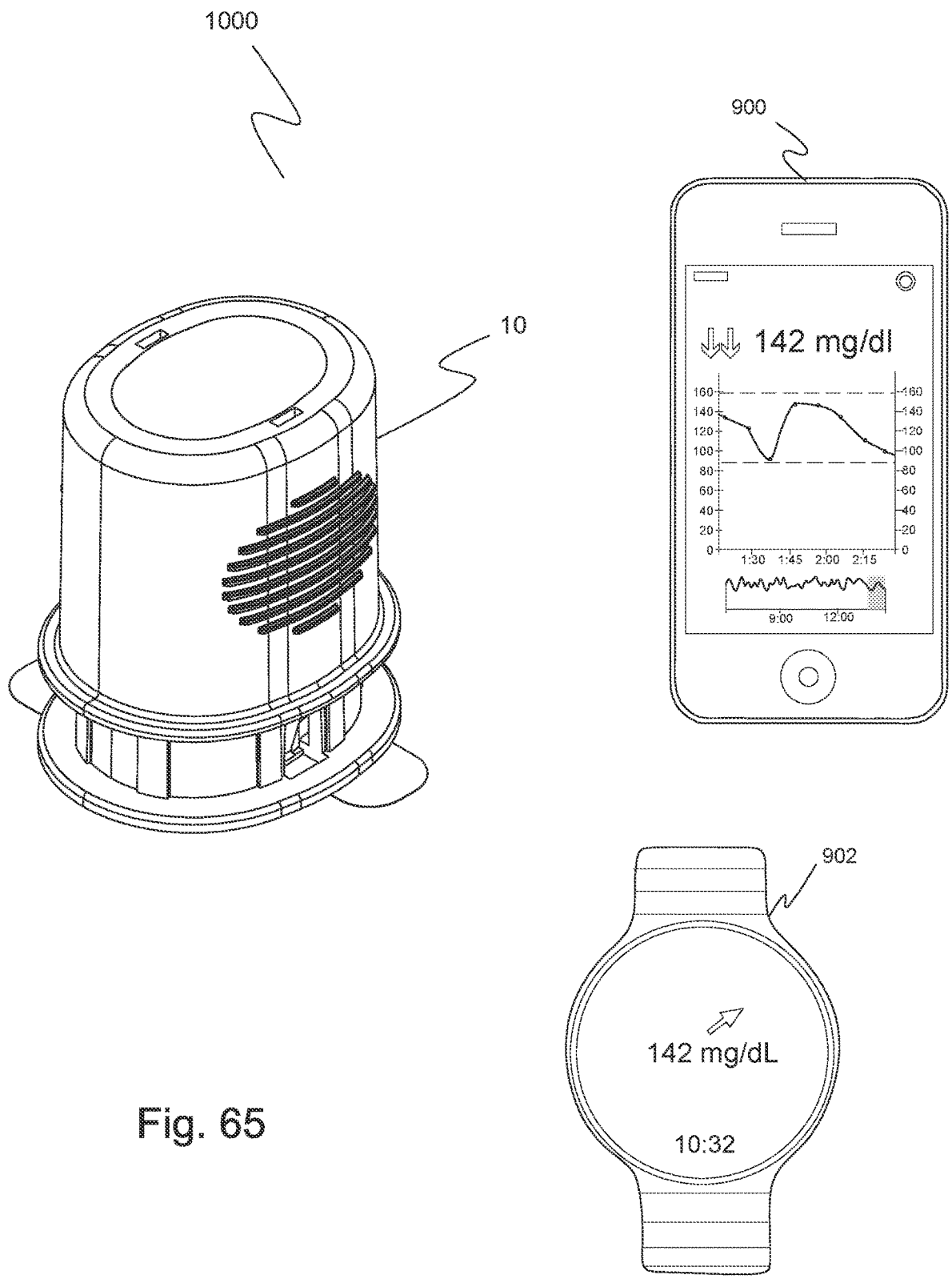
FIG. 65 is a perspective view of one embodiment of a continuous monitoring system of the present invention showing a sensor applicator and display modules.
Figure 66:
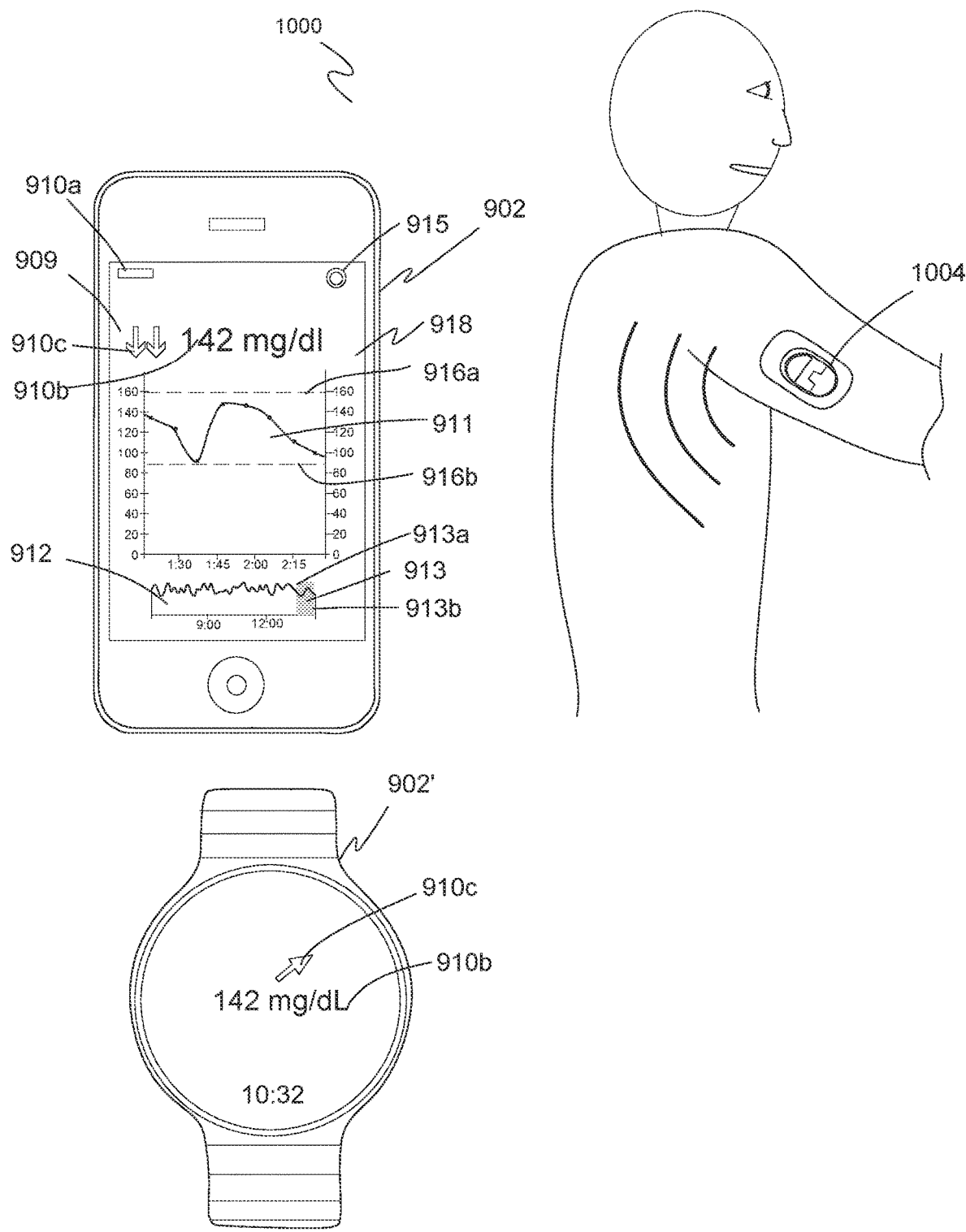
FIG. 66 is a schematic illustration of the continuous monitoring system of the present invention in use.

Referring now to FIGS. 65 and 66, there is illustrated one embodiment of the CGM system 1000 of the present invention. CGM system 1000 includes subcutaneous analyte sensor applicator 10, and an electronic device 900, 902 that is equipped for wireless communication. An adhesive pad 14, which is welded only to a bottom of the sensor lower housing 170 also has an adhesive layer on an opposite side of the adhesive pad 14 where the adhesive layer coincides with the bottom of proximal external body flange portion 27 of applicator housing 21 for adhesively attaching the applicator module 15 to the skin of a patient. This is shown in FIG. 1B.

FIG. 66 shows one embodiment of system 1000 in use after insertion of sensor 250 into the subcutaneous tissue. As shown, FIG. 66 shows examples of electronic device 902, 902', a transmitter 1004 (which is sensor module 160 containing sensor lower housing 170, sensor upper housing 200 and electro-sensor assembly 220) on the patient's arm, where transmitter 1004 communicates analyte measurement data from continuous monitoring sensor 250 (deployed subcutaneously into the patient) to electronic device 902, where the data is displayed to the user on a user interface 918.

System 1000 also includes system software installed on an electronic device 902 equipped for wireless communication with transmitter 1004. Optionally, system 1000 utilizes an analyte strip reader 906 (not shown) for calibration that is capable of wireless communication with electronic device 902. Although a smartphone with software is illustrated, it is understood that the electronic device could be a dedicated reader/meter that is the size of a smartphone or it could be an integrated meter that includes a dedicated continuous glucose monitoring meter integrated with a blood glucose meter for calibration. Examples of electronic device 902 include a computer, a tablet computer, a smartphone, a data logger, a watch, an automobile information/entertainment system, or other electronic device. Wireless communication may be via radio frequency (RF) communication, Wi-Fi, BlueTooth, near-field communication (NFC), a sensor radio, mobile body area networks (MBAN) or other wireless communication protocol. In the embodiment employing a strip reader 906, strip reader 906 has integrated BLE (BlueTooth low energy) and will send calibration data wirelessly to electronic device 902 and query the patient regarding the patient's intention to use the new calibration data point.

In one embodiment, transmitter 1004 communicates to the electronic device 902 using a wireless personal area network (WPAN), such as Bluetooth Low Energy (BLE). In other embodiments, other wireless communication protocols may be used with communication generally effective within a range of a few centimeters to a few meters. In some embodiments, for example, the system software is configured to communicate with Android and/or Apple software platforms installed on mobile phones and the like and has a range of up to thirty feet (about 9.2 meters).

In one embodiment, transmitter 1004 is designed to conserve power and operates via standard Bluetooth BLE protocol. For example, sensor readings from continuous monitoring sensor 250 are transmitted from transmitter 1004 every five minutes and the sensor reading is promptly displayed to the user after being received by the user's electronic device 902. Typically, transmitter 1004 will successfully connect with the electronic device 902 after one or two attempts.

In one embodiment, system 1000 uses universally unique identifier (UUID) filtering to prevent unwanted communication from another device. It is expected that multiple devices may be present and discoverable in proximity to electronic device 902, particularly when the user is in a densely populated area as in a subway, concerts, or other public locations.

In one embodiment, system 1000 utilizes calibration data obtained wirelessly from a separate strip reader. For example, a finger strip reading for glucose is taken and then either manually or automatically entered in system 1000 for calibration. In one embodiment, the system 1000 software application has a means for the user to manually enter a one-point calibration value taken from any meter. For example, the user uses the interface of the electronic device 902 to enter a calibration reading of 100 mg/dl obtained using a separate strip reader. After entering the calibration data, the user can accept, reject, or manually re-enter the calibration data. In other embodiments, the system software receives BLE calibration information from the external meter. After system 1000 receives the calibration data, the user can accept, reject, or manually re-enter this calibration data into the user interface.

The system software provides a user interface 918, one example of which is a touch-sensitive display screen. In one embodiment, user interface 918 has a main screen 909 with indicators 910*a* for radio strength and battery strength. Another indicator 910*b* displays the analyte concentration (e.g., glucose concentration) in units of mg/dL (milligrams per deciliter) or mmol/L (millimoles per liter). Indicator 910*c* displays a glucose trending arrow to communicate to the user whether the analyte concentration (e.g., glucose) is increasing, decreasing, or unchanged. In one embodiment, indicator 910*c* for the trending arrow also communicates the relative rate of change.

In one embodiment, for example, a rate of change having an absolute value equal to or greater than a predefined value (e.g., 3 mg/dL/minute) is displayed as two vertically-oriented arrows (up or down); a rate of change in a second predefined range with an absolute value less than the predefined value (e.g., 2-3 mg/dL/minute is displayed as a single vertically-oriented arrow (up or down); a rate of change in a third predefined range with absolute value less than the second predefined range (e.g., 1-2 mg/dL/minute is displayed as an arrow inclined at 45° to the horizontal (up or down); and a rate of change in a fourth predefined range with an absolute value less than the absolute value of the third predefined range (e.g., 1 mg/dL/minute or less) is displayed as a horizontal arrow to indicate a steady state. In one embodiment, the rate of change is calculated based on five consecutive data points using the following formula:

$$b = \frac{\sum (x - \bar{x})(y - \bar{y})}{\sum (x - \bar{x})^2}$$

In one embodiment, analyte (e.g., glucose) concentration is updated every one minutes with data from transmitter 1004 and displayed on main screen 909. Optionally, transmitted data is updated and stored in transmitter 1004 in case electronic device 902 is out of range or unable to receive during that period. In one embodiment, each transmission by transmitter 1004 includes a predefined number of previous data points (e.g., five) to fill in missing data in the event electronic device 902 is unable to receive during that period.

Main screen 909 also displays a plot 911 of analyte concentration versus time. In one embodiment, the Y-axis (analyte concentration) is configured to automatically scale with a minimum Y-axis value 10% below the minimum value of plotted data and the maximum Y-axis value 10% above the maximum value of plotted data. The X axis may be configured to display a timeframe of the user's choosing.

Main screen 909 also displays a macro timescale 912 of data that includes data displayed in plot 911. Part of the data displayed in macro timescale 912 is highlighted and corresponds to the data displayed in plot 911. For example, macro timescale 912 may be configured to display analyte concentration data over three hours, six hours, twelve hours, twenty-four hours, three days, or one week. Accordingly, data displayed in plot 911 is a subset of data displayed in macro timescale 912. In one embodiment, highlighted area 913 of macro timescale 912 is an active element on user interface 908. For example, by touching highlighted area 913 in the center and dragging left or right, the data of plot 911 is selected and moved. Similarly, by touching highlighted area 913 on left edge 913*a* or right edge 913*b* and dragging left or right, highlighted area 913 is expanded or contracted along the time axis. When the size or location of highlighted area 913 is adjusted, plot 911 is automatically updated to display data between the same minimum time and maximum time of highlighted area 913. Main screen 909 also displays an active service icon 915. Selecting active service icon 915 displays a service screen with indicators 910 for calibration and customization. For example, the service screen includes indicators 910 for setting upper and lower ranges, alarm limits, displayed units, device pairing settings, time scale, X-axis time domain, and the like. For example, the user accesses the service screen to set the time range of data displayed in macro timescale 912 and plot 911. Selecting the calibration icon opens a calibration screen used to calibrate analyte data. In some embodiments, the service screen includes instructions for use or a link to access instructions for use.

For example, user-set or default values for maximum and minimum concentration/control limits are displayed on plot 911 as dashed lines 916*a*, 916*b*, respectively, extending horizontally. In one embodiment, user-set control limits are not alarmed. Default control limits provide upper and lower alert limits and upper and lower reportable range limits. A reading above the maximum 916*a* or below the minimum 916*b* results in an alarm, such as vibration or an audible alert to the user. In one embodiment, maximum concentration limit 916*a* has a default value of 510 mg/dL and minimum concentration limit 916*b* has a default value of 90 mg/dL.

In some embodiments, system software is configured to generate reports for health care professionals. For example, touching an icon opens reports and configurations that could be transferred to a Health Care Professional via the cloud, such as the amount of time above and below target ranges; alarm reports, CGM values; estimated A1C and eAG values, and analyte measurements over time.

In one embodiment, system 1000 enables the user to manually enter a one-point calibration value taken from a separate glucose strip reader. For example, the user enters 100 mg/dl as obtained from a test strip measurement. After entering calibration data, the patient shall accept, reject, or manually re-enter this calibration data into the user interface.

In another embodiment, system 1000 is configured to receive calibration information from strip reader via BLE or other wireless communication protocol.

In some embodiments, settings and preferences may be locked and are accessed only by entering a password, biometric information, or other information serving as a key to unlock the settings and preferences menu.

In one embodiment, system 1000 performs general data calculations using the following generic variable labels:

$$A0=(M*X+B)-(N*Y+C)$$

$$A1=A0+\text{calibration adjustment}$$

$$A2=A1/18.018018$$

$$X=((<\text{channel 0}>*0.000494)-1)*1000$$

$$Y=((<\text{channel 1}>*0.000494)-1)*1000$$

Generic variables are defined as follows:
A0 is uncalibrated CGM value in mg/dL
A1 is calibrated displayed CGM value in mg/dL
A2 is calibrated displayed CGM value in mmol/L (alternate units)
X is the mV reading output of Channel 0 (the sensor signal channel)
M is the slope correction factor Channel 0
B is offset correction factor for Channel 0
Y is the my reading output of Channel 1 (the blank signal channel)
N is the slope correction factor for channel 1
C is the offset correction factor for channel 1

In one embodiment, values for M, B, N, and C variables are stored on electronic device 902. In one embodiment, values A0, A1, X, and Y are stored to a Sqlite Database along with date timestamp. For example, datetime, channel-0-value, channel-1-value, calculated-glucose value, calculated-glucose-value-with-calibration, and device-id. Optionally, a separate database includes patient-entered calibration data with timestamp, such as datetime, entered-calibration value, and device-id.

In one embodiment, values for A1 or A2 (values displayed to the patient in plot 911) that are greater than a predefined maximum limit (e.g., 500 mg/dL or 27.7 mmol/L) result in an error message displayed on user interface 918, such as "Above Reportable Range." Similarly, values for A1 or A2 of less than a predefined minimum limit (e.g., 40 gm/dL or 2.2 mmol/L) result in an error message displayed to the user, such as "Below Reportable Range."

Communication between transmitter 1004 and electronic device 902 is secure. For example, BLE-supported Security Manager Protocol is utilized between transmitter 1004 and electronic device 902. SMP defines the procedures and behavior to manage pairing, authentication, and encryption between the devices, including encryption and authentication, pairing and bonding, key generation for device identity resolution, data signing, encryption, pairing method based on the input/output capabilities of transmitter 1004 and electronic device 902.

In one embodiment, electronic device 902 is a watch configured to communicate wirelessly with transmitter 1004. In such an embodiment, system software includes three screens on the user interface 918 of the electronic device 902' configured as a watch. A first screen displays the most recent analyte concentration and units of measurement. For example, glucose concentration is displayed by indicator 910b in mg/dL or mmol/L and is updated every five minutes. A trending arrow indicator 910c shows the relative rate of change as discussed above.

A second screen displays the most recent glucose concentration and units of measurement. Second screen displays plot 911 with analyte concentration data for the previous one hour, where the Y-axis is glucose concentration and the X-axis is time. Upper and lower limits 916a, 916b are displayed in dashed lines. A third screen displays macro timescale 912 with twenty-four hours of acquired data.

Sensor Construction

Figure 67:
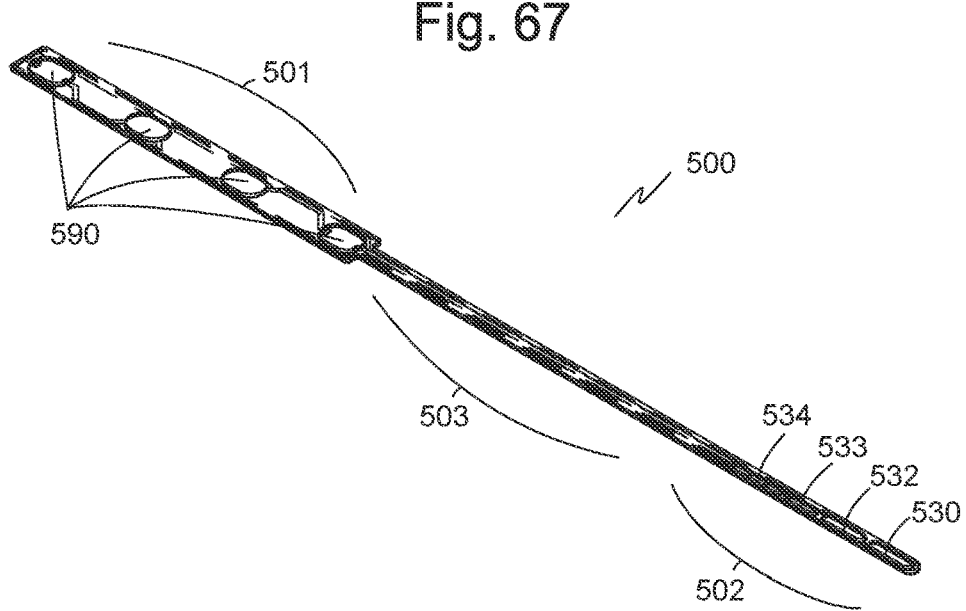
FIG. 67 is a perspective view of one embodiment of a multi-layer sensor.

FIG. 67 shows a perspective illustration of one embodiment of a multi-layer sensor assembly 500 ready for deposition of reagents to create a continuous monitoring sensor 250 having, in this embodiment, a reference electrode 534, a blank or second working electrode 533, a counter electrode 532, and a first working electrode 530. Electrodes 530, 532, 533, 534 are formed at a substrate distal end portion 502 and communicate electrically through assembly middle portion 530 with electrically-conductive contact pads 503 at a substrate proximal end portion 501. Multi-layer sensor substrate 500 is useful to form a subcutaneous analyte sensor, such as a glucose monitoring sensor.

A sensing layer (not shown) is formed over each of the first and second working electrodes 530, 533. The sensing layer is made up of three coating layers, a base coating layer, a second coating layer and a third or top coating layer. The base coating layer contains poly-2-hydroxyethyl methacrylate (PHEMA) and is the coating that is disposed directly on the exposed metal at the bottom of the respective wells at substrate distal end portion 502. Specific to the first working electrode where glucose is measured, glucose oxidase and/or glucose dehydrogenase is also included. The second working or blank electrode does not contain any enzyme and is used only for measuring background noise and/or interferents in the sample since the first working electrode will have a total current that include a portion driven by the amount of glucose in the subcutaneous tissue as well as the background noise and/or interefents derived current. Using an algorithm to subtract the current derived from the second working or blank electrode from the first working electrode provides a more accurate glucose measurement. The second coating layer is disposed directly on the base coating layer and contains PHEMA and a plurality of microspheres from polydimethylsiloxane (PDMS). PDMS is a material a material having substantially no or little permeability to glucose but a substantially high permeability to oxygen. The third or top coating layer is disposed directly on the second coating layer and contains PHEMA and catalase. Catalase is a material that prevents release of hydrogen peroxide from the sensing layer into the surrounding environment. In this case, the surrounding subcutaneous tissue. For the reference electrode 534, a silver-silver chloride (AgCI) layer is created on the metal at the bottom of the well and then the AgCI layer is covered with a hydrogel membrane. The counter electrode 532 has the metal at the bottom of the well covered only with a hydrogel membrane.

Figure 68:
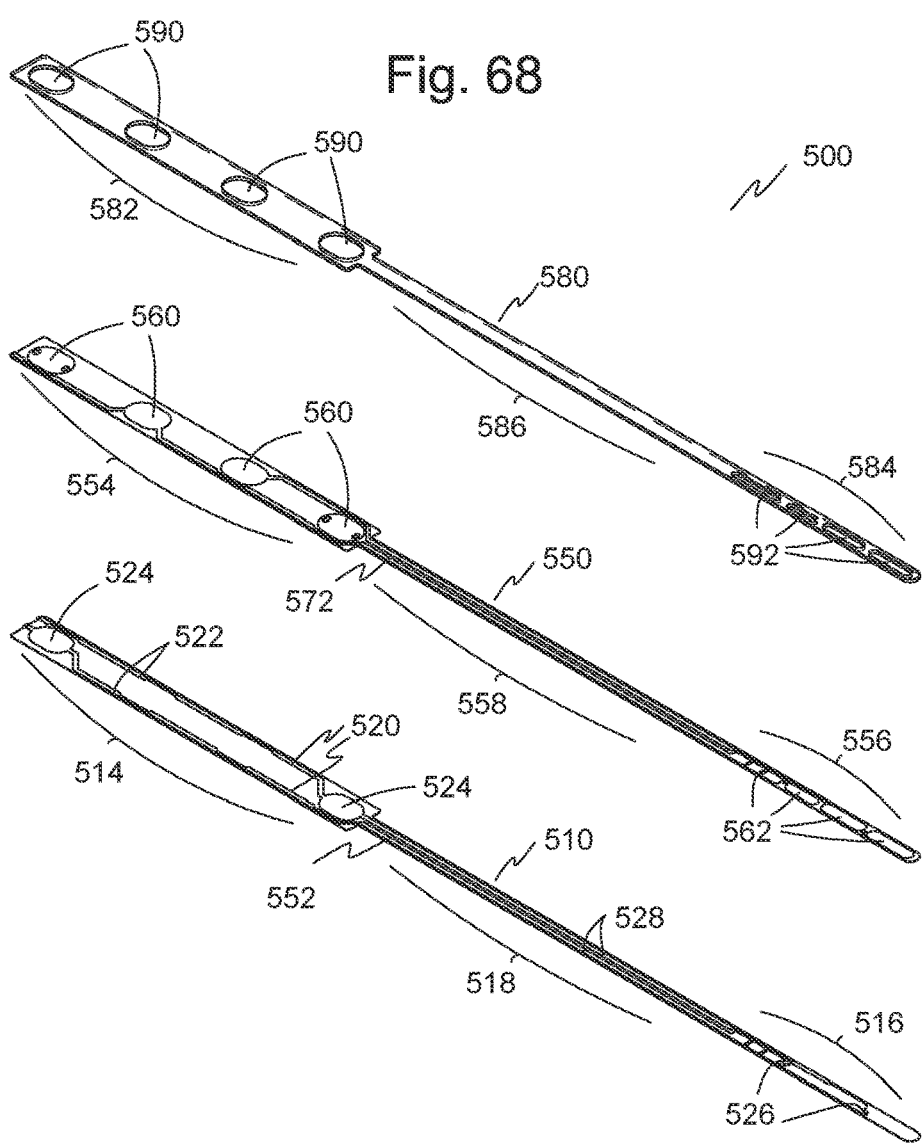
FIG. 68 is an exploded perspective view of the multi-layer sensor of FIG. 67 showing a base layer, a middle layer and a top layer.

Referring now to FIG. 68, a perspective, exploded illustration shows a base layer 510, a middle layer 550, and a top layer 580 that together comprise multi-layer sensor substrate 500. "Middle layer" herein means the layer adjacent to the top layer 580 without any intervening, electrically-insulating layer when there are other layers between base layer 510 and middle layer 550. Base layer 510 is electrically insulating and includes a base proximal end portion 514, a base distal end portion 516, and a base middle portion 518 between base proximal end portion 514 and base distal end portion 516. A base metallized layer 520 is disposed on base layer 510 and defines at least one circuit 552 extending longitudinally along base layer 510. Each circuit 552 has an electrically-conductive contact pad 524 formed at base proximal end portion and an electrically-conductive contact pad 526 formed at base distal end portion 516 with an electrically-conductive trace 528 electrically coupling electrically-conductive contact pad 524 at the base proximal end 514 with electrically-conductive pad 526 at base distal end 516.

Middle layer 550, also electrically insulating, is disposed over base layer 510 and includes a middle layer proximal end portion 554, a middle layer distal end portion 556, and a middle layer middle portion 558. Middle layer 550 has a size and shape corresponding to base layer 520 and that is aligned with base layer 510. Middle layer 550 includes electrically-conductive contact pads 560 at middle layer distal end portion 556 adapted to receive an electrode material or reagent to form a respective electrode. Each electrically-conductive contact pad 562 at middle layer proximal end portion 554 is adapted to receive an electrical contact.

The top layer 580, also electrically-insulating, is disposed over middle layer 550. Top layer 580 has a size and shape corresponding to middle layer 550 and base layer 510. Top layer 580 has a top layer proximal end portion 582, a top layer distal end portion 584, and a top layer middle portion 586, where top layer 580 aligned with base layer 510 and middle layer 550. Top layer 580 has a plurality of openings that include contact openings 590 on substrate proximal end portion 501 and sensor wells 592 on substrate distal end portion 502. Contact openings 590 and sensor wells 592 coincide with electrically-conductive contact pads 560, 562, respectively, of middle layer 550. Base layer 510, middle layer 550, and top layer 580 are manufactured with circuits 552, 572 on base layer 510 and middle layer 550 to create multi-layer sensor substrate 500 with substrate proximal end portion 501, substrate distal end portion 502, and assembly middle portion 503 extending longitudinally between substrate proximal end portion 501 and substrate distal end portion 502 as shown, for example, in FIG. 42. Substrate distal end portion 502 and assembly middle portion 503 each have a width of about 279 microns.

Referring now to FIGS. 69-71, base layer 510 is shown in a plan view in FIG. 44, base proximal end portion 514 is shown enlarged in FIG. 70, and base distal end portion 516 is shown enlarged in FIG. 71. Base layer 510 has a base layer substrate 512 that is electrically insulating and includes a base proximal end portion 514, a base distal end portion 516, and a base middle portion 518 extending between and connecting base proximal end portion 514 and base distal end portion 516. In one embodiment, base layer substrate 512 is made of polyimide and has a thickness from 7.5 μm to 12.5 μm. For example, base layer substrate 512 has a thickness of about 10 μm. In one embodiment discussed in more detail below, base layer substrate 512 may be formed by spin coating polyimide on a glass plate followed by further lithographic processing.

Base metallized layer 520 is disposed directly onto base layer substrate 512 and defines at least one circuit extending longitudinally along base layer substrate 512 from base layer proximal end portion 514 to base layer distal end portion 516. In one embodiment as shown, base metallized layer 520 defines two circuits 522, where each circuit 522a, 522b has an electrically-conductive contact pad 524a, 524b, respectively, formed at base proximal end portion 514. Circuit 522a has an electrically-conductive contact pad 526a1-526a2, formed at base distal end portion 516. Circuit 522b has electrically-conductive contact pad 526b at distal end portion 516. Each circuit 522a, 522b has an electrically-conductive trace 528 (528a and 528b) electrically coupling electrically-conductive contact pad 524a1-524a2, 524b at the base proximal end portion 514 with the respective electrically-conductive pad 526a, 526b at the base distal end portion 516. For example, circuit 522a is configured for a working electrode 530 of sensor assembly 500 and circuit 522b is configured for a blank electrode 533 of sensor assembly 500 (shown in FIG. 67).

Contact pads 526a1-526a2 each have a size and shape corresponding to one or more contact pads 562 of middle metallized layer 550, rather than being sized only for through openings 564 of middle layer substrate 552. An advantage of this configuration is that contact pads 526a1-526a2 reduce stress induced to contact pads 562 caused by the spin coating process described below, which stress leads to cracking of contact pads 562 in middle metallized layer 570. In one embodiment, for example, contact pad 526a1 is sized and shaped to substantially underlie contact pad 562a of middle metallized layer 570, but not through opening 564c. Contact pad 526a2 is sized and shaped to substantially underlie contact pads 562b, 562c and through opening 564d of middle metallized layer 570.

In one embodiment, base metallized layer 520 has an overall thickness of 1200±300 Å. For example, base metallized layer 520 is formed by depositing a first part of chromium (200±150 Å) directly onto and against base layer substrate 512, a second part of gold (1000±150 Å) disposed directly onto the chromium, and a third part of chromium (200±150 Å) disposed directly onto the gold. In other words, the base metallized layer 520 has a thickness in the range of about 900 Angstroms to about 1,500 Angstroms. Other conductive materials and thicknesses are acceptable for base metallized layer 520 depending on the intended use of sensor assembly 500.

Figure 72:
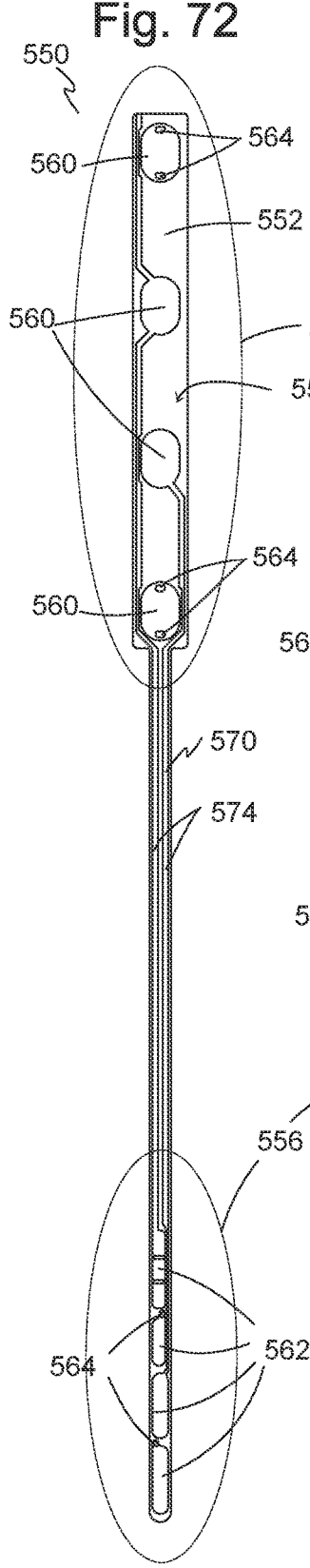
FIG. 72 is a plan view of the sensor of FIG. 67 showing the middle layer only with an electrical contact portion and a sensor end portion circled.
Figure 73:
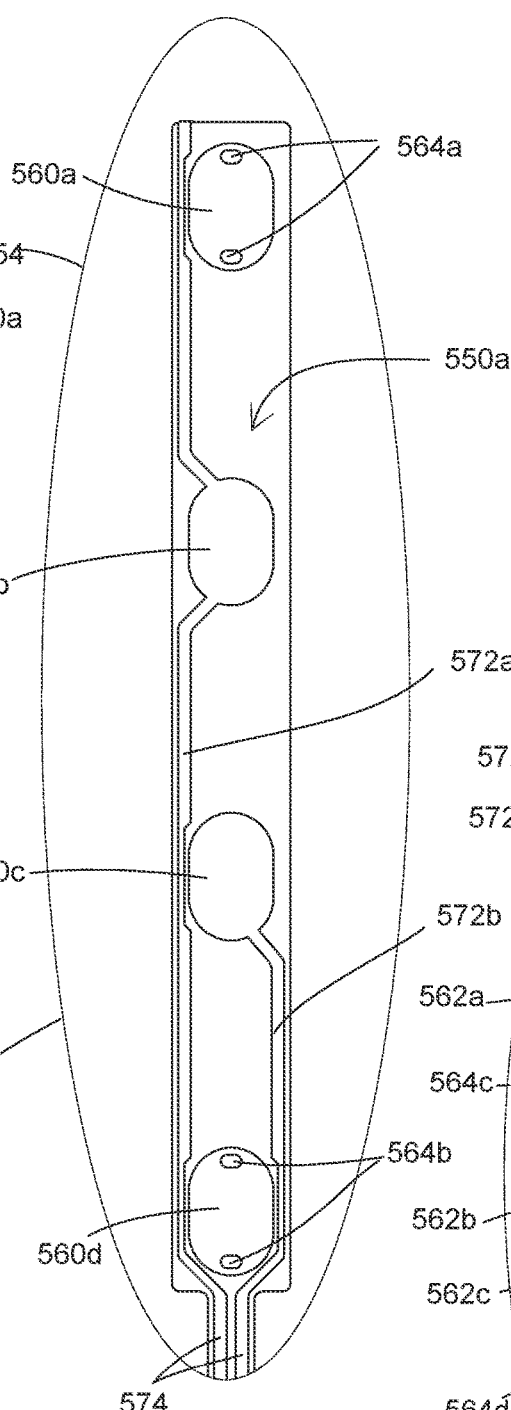
FIG. 73 is an enlarged view of the electrical contact portion of FIG. 72.

Referring now to FIGS. 72-74, middle layer 550 is shown in a plan view in FIG. 72, second proximal end portion 554 is shown enlarged in FIG. 73, and second distal end portion 556 is shown enlarged in FIG. 74. Middle layer 550 has a middle layer substrate 552 that is electrically insulating and defines a plurality of middle layer through openings 564 with side walls extending to base layer 510, where each middle layer through opening 564 communicates electrically with a respective electrically-conductive contact pad 524, 526 of circuit 552 of base layer 510. In one embodiment, middle layer substrate 552 is made of polyimide that is spin coated onto base layer 510 and base metallized layer 520 as discussed below, for example, in a method 600 of making multi-layer sensor substrate 500.

In one embodiment, middle layer substrate 552 has a thickness from 7.5 μm to 12.5 μm, such as about 10 μm.

A middle metallized layer 570 is disposed directly onto middle layer substrate 552 and the side walls of through openings 564 to define at least two middle layer circuits 572, where each middle layer circuit 572 has electrically-conductive contact pad 560 formed at middle layer proximal end portion 554 and electrically-conductive contact pad 562 formed at middle layer distal end portion 556 with an electrically-conductive trace 574 electrically coupling contact pad 560 at middle layer proximal end portion 554 with electrically-conductive contact pad 562 at middle layer distal end portion 556, and a least one or more additional electrically conductive pads 560, 562 in electrical contact with through openings 564. The at least one or more additional electrically conductive pads 560, 562 electrically coupled to base layer circuit(s) 552 by way of through openings or vias 564. For example, middle metallized layer 570 is deposited on top surface 550a, on the sidewalls of through openings 564, and onto part of base metallized layer 520 creating electrical continuity between the base metallized layer 520 and the respective contact pads 560, 562.

In one embodiment of middle layer proximal end portion 554 as shown in FIG. 73, for example, middle layer circuit 572a includes contact pad 560b and middle layer circuit 572b includes contact pad 560c. Contact pads 560a, 560d are isolated from middle layer circuits 572a, 572b. Contact pad 560a (e.g., for working electrode 130) defines two through openings 564a and contact pad 560b (e.g., for blank electrode 133) defines two through openings 564b, each of which has electrical continuity to base metallized layer 520 at contact pad 524a and contact pad 524b, respectively (shown in FIG. 70).

In one embodiment of middle layer distal end portion 556 as shown in FIG. 74, for example, middle layer circuit 572a includes contact pad 562a and middle layer circuit 572b includes contact pad 562c. Contact pads 562b, 562d are isolated from middle layer circuits 572a, 572b. Middle layer substrate 552 has through opening 564c at with contact pad 562b (e.g., for blank electrode 133) having electrical continuity to base metallized layer 520 at contact pad 526b (shown in FIG. 71). Middle layer substrate 552 defines through opening 564d with contact pad 562d having electrical continuity with contact pad 526a2 (shown in FIG. 71). Contact pads 562d and 562b are isolated from middle layer circuits 572a, 572b. Contact pad 562a (i.e. the reference electrode 134) is segmented into 3 contact pad portions 562a1, 562a2 and 562a3. The reference electrode 534 is segmented to prevent cracking of the Ag/AgCl and delamination from contact pad 562a, which is a definite advantage where sensor 500 is implanted subcutaneously in a patient.

An advantage of the multi-layer sensor assembly 500 is the ability to construct a sensor having a smaller width that penetrates the subcutaneous tissue than is achievable by laying all of the conductive traces side-by-side on a single substrate. The multi-layer sensor assembly 500 uses multiple layers for the traces thus reducing the width by limiting each layer to one or two circuit traces.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An all-inclusive, single-use, subcutaneous analyte sensor applicator and monitoring system (10) comprising:
    an applicator module (15) having a vertical axis (L1) comprising:
        an applicator housing (21) having an applicator circumferential wall (25) forming an applicator body (22) and defining an applicator housing chamber (28), an inwardly-facing applicator housing retaining arm (30) adjacent a proximal body end (24), and a proximal external body flange portion (27) disposed at the proximal body end (24);
        a deployment button (50) defining a button chamber (58) and a button retaining arm (60) wherein the applicator housing (21) is partially received within the button chamber (58);
        a pre-loaded insertion assembly (100) completely disposed and secured within the button chamber (58) and partially disposed within the applicator housing chamber (28) when the deployment button (50) is in an initial loaded position, the pre-loaded insertion assembly (100) comprising:
            an insertion assembly housing (110) defining an assembly housing chamber (118), and an assembly housing retaining arm (120) formed in the insertion assembly housing (110), the assembly housing retaining arm (120) having an outward-facing housing arm hook surface (121) wherein the assembly housing retaining arm (120) interacts with the applicator housing (21) to move from the initial loaded position to a second, locked position when the deployment button (50) is activated;
            a biasing element (149) disposed within the assembly housing chamber (118); and
            a needle assembly (140) comprising:
                a needle (155); and
                a needle body (142) having a needle body retaining arm (150) with an outward-facing needle retaining arm hook surface (151) formed in the needle body (142), and a needle receiving portion (154) formed in the needle body (142) wherein the needle (155) extends parallel to the vertical axis (L1) a predefined distance beyond the needle body (142) defining a needle axis (L2) and wherein the biasing element (149) is positioned against the needle body (142) and the insertion assembly housing (110) wherein the biasing element (149) is in a compressed state when the deployment button (50) is in the initial loaded position and a less compressed state when the deployment button (50) is in the second, locked position;
        a sensor module (160) comprising:
            a sensor lower housing (170) having a lower housing opening (176) adapted for receiving the needle (155) therethrough when the deployment button (50) is activated and a power actuator (175), the sensor lower housing (170) being releasably connected to the applicator housing (21) by the applicator housing retaining arm (30);
            a sensor upper housing (200) having an upper housing top (205) with a housing top opening (206) through which the needle (155) extends, the sensor upper housing (200) removably retained against the insertion assembly housing (110) and spaced from the sensor lower housing (170); and
            an electro-sensor assembly (220) disposed within the sensor upper housing (200), the electro-sensor assembly (220) having an electronic circuit (230) with a power switch (240) and a sensor (250) electrically coupled to the electronic circuit (230) wherein the sensor (250) is temporarily disposed within the needle (155) when the deployment button (50) is in the initial loaded position; and
        a single-sided adhesive pad (14) having a non-adhesive side welded to the sensor lower housing (170);
    wherein the applicator system (10) is preassembled and ready to use because no assembly is required of any portion of the sensor module (160) and/or the electro-sensor assembly (230) to the applicator module (15) and no other manipulation of the system (10) to power the electronic circuit (230) is required by a user other than a single activation of the deployment button (50)

by the user to insert the sensor (250) subcutaneously in a host, which activation causes the applicator system (10) to perform the following at substantially simultaneously at the same time: to assemble the sensor module (160) as a single unit, to insert the sensor (250) subcutaneously, to retract the needle assembly (140), to turn on the power switch (240) to the electro-sensor assembly (220), to release the sensor module (160) from the applicator module (15), and to release the applicator module (15) from the surface of the skin.

2. The system of claim 1 wherein the applicator housing (21) has a proximal internal body flange portion (26) adjacent the proximal applicator housing end (24).

3. The system of claim 1 wherein the deployment button (50) has a button elongated body (52) defining the button chamber (58), a closed button distal end (53) and the button retaining arm (60) extends within the button chamber (58) from the closed button distal end (53) toward an open button proximal end (54) a predefined distance.

4. The system of claim 1 wherein the assembly housing (110) has an assembly housing body (112) having an assembly circumferential wall (111) defining the assembly housing chamber (118), a closed housing proximal end (114), a recessed housing bottom (115) at the closed housing proximal end (114), an open housing distal end (113), the assembly housing retaining arm (120) formed in the assembly circumferential wall (111) and extending toward the closed housing proximal end (113), a plurality of housing retaining fingers (124) formed in the assembly circumferential wall (111) and extending toward and beyond the closed housing proximal end (113) and having an inward-facing housing finger hook surface (125), an assembly housing locking slot (130) that interacts with the button retaining arm (60) to secure the pre-loaded insertion assembly (100) within the button chamber (58), and a needle assembly locking slot (132) that interacts with the needle body retaining arm (150).

5. The system of claim 1 wherein the biasing element (149) is positioned on one end against a recessed housing bottom (115) of the assembly housing (110).

6. The system of claim 1 wherein the needle body (142) has a needle body circumferential wall (141), a closed needle body distal end (143) forming a needle body top (145), an open needle body proximal end (144) wherein the needle body retaining arm (150) is formed in the needle body circumferential wall (141) to thereby position the outward-facing needle retaining arm hook surface (151) adjacent to the closed needle body distal end (143), and a needle receiving portion (154) formed in the needle body top (145) wherein the needle (155) is secured adjacent the needle distal end (156) and extends parallel to the needle body circumferential wall (141) a predefined distance beyond the open needle body proximal end (144) and wherein the biasing element (149) is positioned against the closed needle body distal end (143) through the open needle body proximal end (144).

7. The system of claim 1 wherein the sensor lower housing (170) has a plurality of lower housing locking elements (174) extending upward a predefined distance from a lower housing bottom (172) into the applicator housing chamber (28).

8. The system of claim 1 wherein the sensor lower housing (170) has a lower housing locking recess (178) in a lower housing wall (172) wherein the applicator housing retaining arm (30) engages the lower housing locking recess (178) when the deployment button (50) is in the initial pre-loaded position.

9. The system of claim 1 wherein the sensor upper housing (200) has an upper housing circumferential wall (202) extending from the upper housing top (205) forming a housing top flange portion (208) in a perimeter of the upper housing top (205), the upper housing circumferential wall (202) having a plurality of upper housing locking recesses (204) adapted for mating connection to a plurality of locking elements (174) of the sensor lower housing (170).

10. The system of claim 1 wherein the electro-sensor assembly (220) includes a battery (235) coupled between the electronic circuit (230) and the power switch (240).

11. The system of claim 1 further comprising an electronic device (902) containing software for wireless communication with sensor module (160).

12. A method of inserting a sensor subcutaneously, the method comprising:
providing the all-inclusive, single-use, subcutaneous analyte sensor applicator and monitoring system (10) of claim 1; placing the all-inclusive, single-use, subcutaneous analyte sensor applicator and monitoring system against a skin of the patient; and actuating the system (10) wherein the actuating step causes substantially simultaneously the automatic assembling of the sensor module (160) as a single unit against the skin of the patient, implanting the sensor (250) subcutaneously, automatically powering the electronic circuit (230), and automatically separating the applicator module (15) from the assembled sensor module (160) and from the skin of the patient.

13. The method of claim 12 wherein the providing step includes removing an adhesive tape cover (12) from an applicator housing assembly (20) before the placing step.

14. The method of claim 12 wherein the actuating step includes pushing a deployment button (50) from an initial pre-loaded position on an applicator housing assembly (20) toward the skin of the animal such that a needle (155) containing a sensor (250) penetrates the skin and inserts the sensor (250) leaving the sensor (250) deployed while the needle (155) completely retracts into an assembly housing (110) located within the deployment button (50) while the deployment button (50) locks into a second position on the applicator housing assembly (20).

15. The method of claim 12 wherein the providing step includes providing a single-sided adhesive pad (14) having an adhesive pad opening (14a) and a non-adhesive side wherein a portion of the non-adhesive side is welded to a lower housing bottom (172) of a sensor lower housing 170 of the sensor module (160) before the placing step such that the pad opening (14a) of the adhesive pad (14) is aligned with a needle axis (L2) of a needle (155).

16. A method of making an all-inclusive, single-use, subcutaneous analyte sensor applicator and monitoring system (10), the method comprising:
forming each of the following:
(a) an applicator housing (21) defining an applicator housing chamber (28) and an applicator housing retaining arm (30);
(b) a deployment button (50) defining a button chamber (58) and a button retaining arm (60);
(c) an assembly housing (110) defining an assembly housing chamber (118), an assembly housing retaining arm (120) formed in the assembly housing (110) and having an outward-facing housing arm hook surface (121);
(d) a biasing element (149);
(e) a needle assembly (140) having a needle body (142) and a needle (155) fixedly attached to the needle body (142) wherein the needle (155) extends a predefined distance beyond the needle body (142) defining a needle axis (L2);

(f) a sensor lower housing (170) having a power actuator (175) and a lower housing opening (176) adapted for receiving the needle (155);

(g) a sensor upper housing (200) having an upper housing top (205) with a housing top opening (206); and (h) an electro-sensor assembly (220) having an electronic circuit (230) with a power switch (240) and a sensor (250) electrically coupled to the electronic circuit (230);

disposing the biasing element (149) within the assembly housing chamber (118) of the assembly housing (110);

inserting the needle assembly (140) within the assembly housing chamber (118) so that the needle body (142) contacts the biasing element (149) and then pushing the needle body (142) into the assembly housing chamber (118) to compress the biasing element (149) until a needle body retaining arm (150) locks into a needle assembly locking slot (132) of the assembly housing (110) such that the needle (155) extends beyond a closed housing proximal end 114 and through a housing proximal end opening (116);

inserting the combined needle assembly (140), the biasing element (149) and the assembly housing (110) into the button chamber (58) of the deployment button (50) until the button retaining arm (60) of the deployment button (50) locks into an assembly housing locking slot (130) of the assembly housing (110);

attaching the sensor upper housing (200) to the assembly housing (110) containing the needle assembly (140) and the biasing element (149) such that a needle (155) of the needle assembly (110) extends through an upper housing top opening (206) of the sensor upper housing (200);

inserting the electro-sensor assembly (220) into the sensor upper housing (200) such that the sensor (250) is positioned within the needle (155) wherein the assembly housing (110), the biasing element (149), the needle assembly (140), the sensor upper housing (200), and the electro-sensor assembly (220) form a pre-loaded insertion assembly (100);

attaching the sensor lower housing (170) to an open proximal body end (24) of the applicator housing (21); and inserting a portion of the applicator housing (21) into the button chamber (58) a predefined distance such that an applicator body circumferential wall (25) at an open distal body end (22) of the applicator housing (21) slides between the assembly housing (110) and the deployment button (50) until an assembly housing retaining arm (120) catches into a distal applicator housing notch (32) in applicator body circumferential wall (25).

17. The method of claim 16 further comprising attaching a single-sided adhesive tape (14) having a pad opening (14a) to the open proximal body end (24) of the applicator housing (21) such that the pad opening (14a) of the adhesive tape (14) is aligned with the needle axis (L2).

\* \* \* \* \*